United States Patent
Kulcke et al.

(10) Patent No.: US 11,025,843 B2
(45) Date of Patent: Jun. 1, 2021

(54) DEVICE AND METHOD FOR THE CONTINUOUS AND NON-INVASIVE DETERMINATION OF PHYSIOLOGICAL PARAMETERS OF A TEST SUBJECT

(71) Applicant: OXY4 GmbH, Pepelow (DE)

(72) Inventors: Axel Kulcke, Pepelow (DE); Amadeus Holmer, Rostock (DE)

(73) Assignee: Cinogy GmbH, Duderstadt (DE)

(*) Notice: Subject to any disclaimer, the term of this patent is extended or adjusted under 35 U.S.C. 154(b) by 5 days.

(21) Appl. No.: 16/068,843

(22) PCT Filed: Jan. 6, 2017

(86) PCT No.: PCT/EP2017/050272
§ 371 (c)(1),
(2) Date: Jul. 9, 2018

(87) PCT Pub. No.: WO2017/118735
PCT Pub. Date: Jul. 13, 2017

(65) Prior Publication Data
US 2019/0028662 A1 Jan. 24, 2019

(30) Foreign Application Priority Data
Jan. 8, 2016 (EP) .................................... 16150553

(51) Int. Cl.
*H04N 5/355* (2011.01)
*A61B 5/00* (2006.01)
(Continued)

(52) U.S. Cl.
CPC ....... *H04N 5/35554* (2013.01); *A61B 5/0205* (2013.01); *A61B 5/02416* (2013.01);
(Continued)

(58) Field of Classification Search
CPC .. H04N 5/35554; H04N 5/3452; H04N 5/332; A61B 5/02416; A61B 5/7257;
(Continued)

(56) References Cited

U.S. PATENT DOCUMENTS

2008/0097173 A1 4/2008 Soyemi et al.
2009/0326347 A1 12/2009 Scharf
(Continued)

FOREIGN PATENT DOCUMENTS

WO WO-2004/097365 A2 11/2004
WO WO-2010/053617 A2 5/2010
(Continued)

OTHER PUBLICATIONS

International Application No. PCT/EP2017/050272, International Search Report (English translation), dated Jan. 8, 2018.

*Primary Examiner* — Mark Bockelman
(74) *Attorney, Agent, or Firm* — W&C IP

(57) ABSTRACT

The present invention relates to a device for the non-invasive determination of physiological parameters of a test person with a lighting unit (32), having a plurality of LED types whose emission maxima are at different wavelengths from the visible to the NIR wavelength range and include an emission maximum below 590 nm, a photo sensor for application to the skin, a data processing unit (11) for reading out the photo sensor and for controlling the illumination unit (32), so that the different types of LEDs individually in a predetermined activation sequence at successive activation start times $t_k$ (k=1, 2 ... M) are activated for a respective predetermined activation period, and to repeat the activation sequence with a clock frequency as a result n=1, 2 ... N, wherein the clock frequency—sufficiently high for the resolution of the pulse—is characterized in that the photo sensor is a camera sensor (34) on CCD or CMOS base, which is arranged to the illumination unit (32) in a way that
(Continued)

Figure 1:
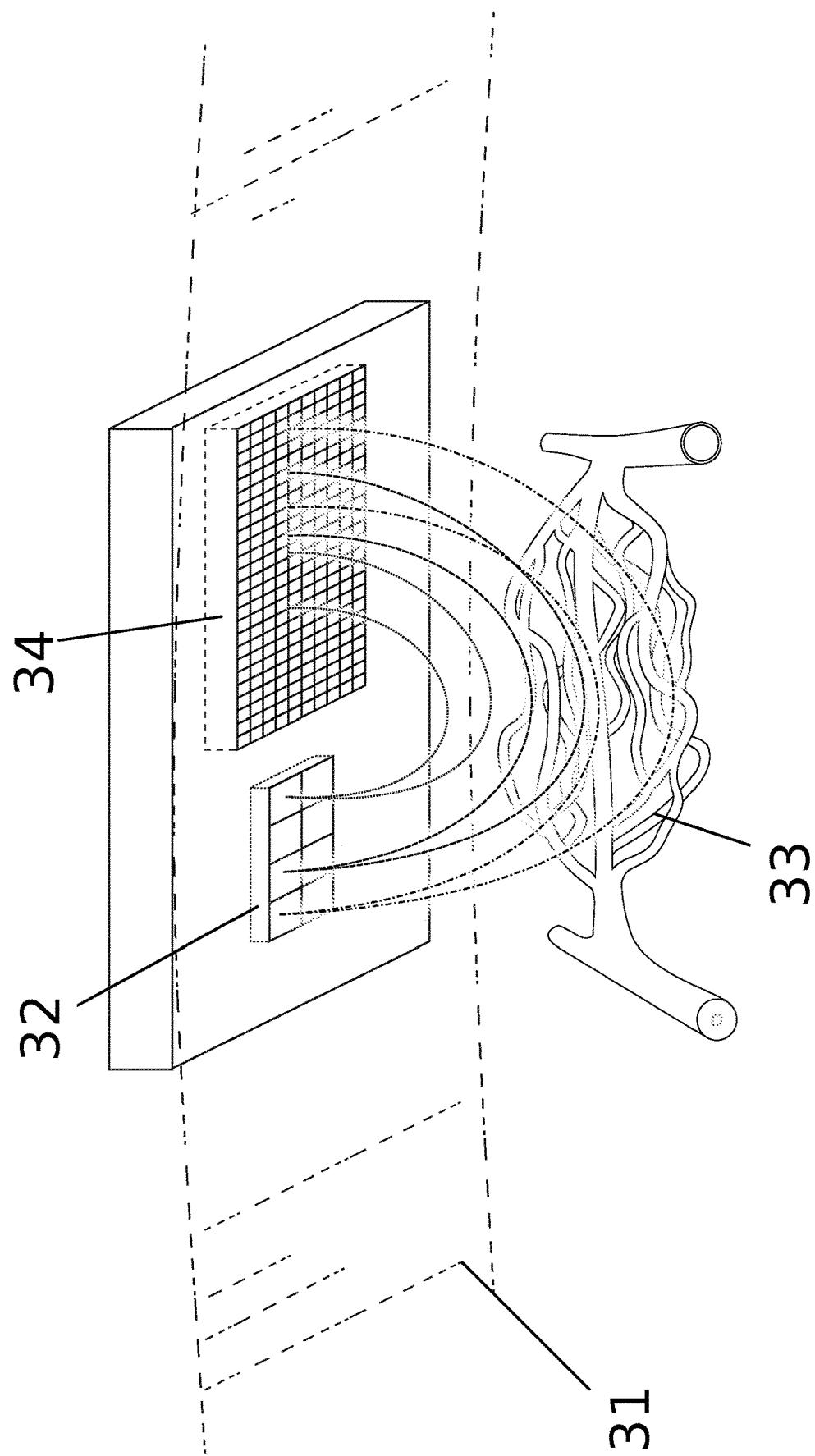

it can detect by transflection light passing through the body, that the data processing unit (11) reads out the camera sensor in each activation sequence at the activation start times $t_k$ (k=1, 2 . . . M) and over the respective activation period, with the detected intensities via subregions of sensor elements being added up and assigned to the respective activation sequence and to the respective activation start time $t_k$ (k=1, 2 . . . M), and records them as time series, wherein subareas of the camera sensor are added up by reading out the lines of the camera sensor, which are parallel to the connection axis between the illumination unit and the camera sensor and along which increases the distance from the illumination unit, and parallel lines are summarized to a single averaged line, and the data processing device is arranged to evaluate the averaged line as a function of the distance from the illumination unit to the muscle oximetry.

15 Claims, 10 Drawing Sheets

(51) Int. Cl.
| | | |
|---|---|---|
| *A61B 5/1455* | (2006.01) | |
| *H04N 5/33* | (2006.01) | |
| *A61B 5/0205* | (2006.01) | |
| *A61B 5/024* | (2006.01) | |
| *H04N 5/345* | (2011.01) | |
| *A61B 5/08* | (2006.01) | |

(52) U.S. Cl.
CPC ........ *A61B 5/14552* (2013.01); *A61B 5/4519* (2013.01); *A61B 5/4872* (2013.01); *A61B 5/4875* (2013.01); *A61B 5/4884* (2013.01); *A61B 5/7257* (2013.01); *H04N 5/332* (2013.01); *H04N 5/3452* (2013.01); *A61B 5/02433* (2013.01); *A61B 5/02438* (2013.01); *A61B 5/0816* (2013.01); *A61B 2503/10* (2013.01); *A61B 2562/0238* (2013.01)

(58) Field of Classification Search
CPC ... A61B 5/4884; A61B 5/4875; A61B 5/4872; A61B 5/4519; A61B 5/0205; A61B 5/14552; A61B 2503/10; A61B 2562/0238; A61B 5/0816; A61B 5/02438; A61B 5/02433
See application file for complete search history.

(56) References Cited

U.S. PATENT DOCUMENTS

| | | |
|---|---|---|
| 2012/0253153 A1 | 10/2012 | Trumble |
| 2014/0016132 A1 | 1/2014 | Schmitz |
| 2015/0196238 A1 | 7/2015 | Dacso et al. |
| 2015/0282724 A1 | 10/2015 | McDuff et al. |
| 2015/0282746 A1 | 10/2015 | Yousefi et al. |
| 2015/0297133 A1 | 10/2015 | Jouanique-Dubuis et al. |
| 2016/0022147 A1 | 1/2016 | Kulcke |

FOREIGN PATENT DOCUMENTS

| | | |
|---|---|---|
| WO | WO-2010/093865 A1 | 8/2010 |
| WO | WO-2011/091280 A2 | 7/2011 |
| WO | WO-2013/158459 A1 | 10/2013 |
| WO | WO-2014/139830 A1 | 9/2014 |

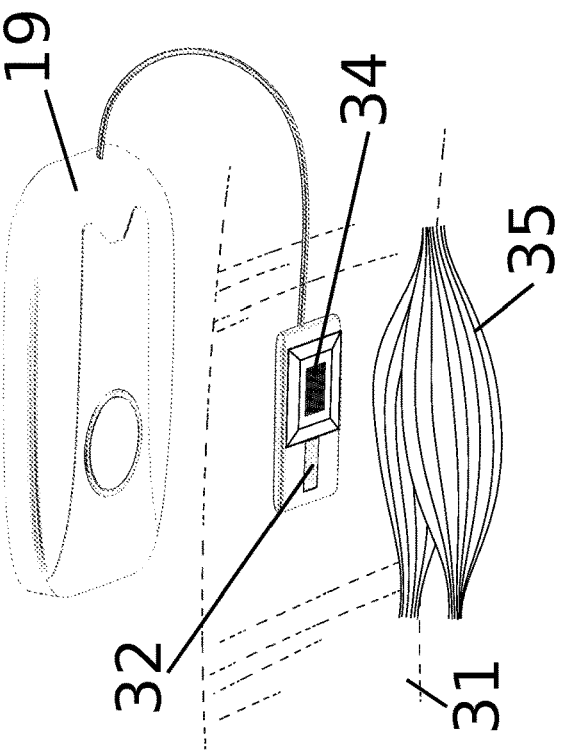
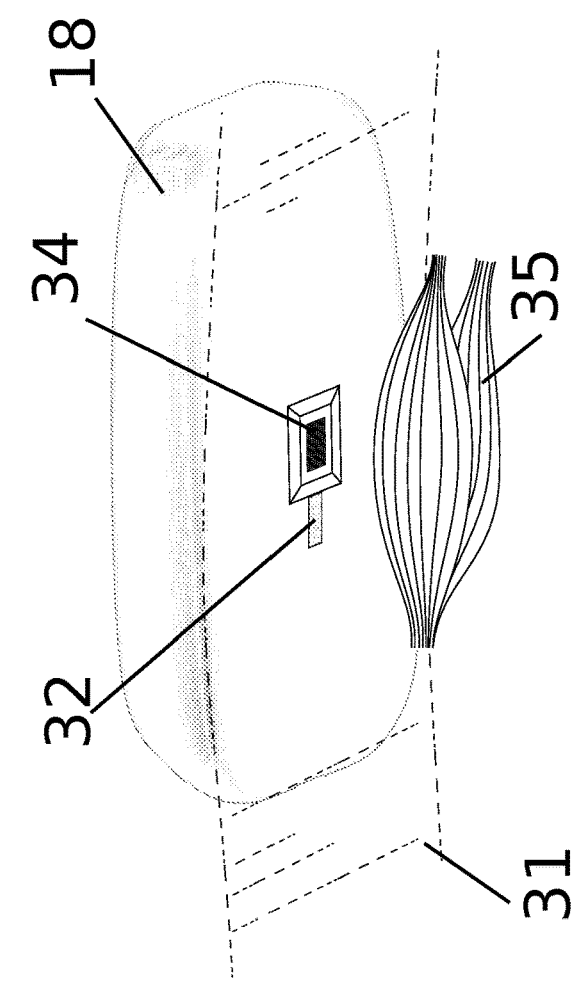
Fig. 5

DEVICE AND METHOD FOR THE CONTINUOUS AND NON-INVASIVE DETERMINATION OF PHYSIOLOGICAL PARAMETERS OF A TEST SUBJECT

The present invention relates to a device for the continuous and non-invasive determination of physiological parameters of a test person under physical activity, comprising:

an LED-based illumination unit designed to rest on the skin of the test person at a desired measuring point with a majority of different LED types arranged next to each other, the emission maxima of which are at different wavelengths $\lambda 1, \lambda 2 \ldots \lambda L$ from the visible to the NIR-wavelength range;

a photo sensor which is designed to rest on the test person's skin in order to capture light which is emitted by the illumination unit and passes through the test person's body towards an exit place in the area of the photo sensor; and a data processing unit, which is connected to the photosensor to read it out and which is connected to the lighting unit and which is configured to activate the different LED-types individually in a specified activation sequence at successive activation starting times $t_k$ (k=1, 2 . . . M) for a respective predetermined activation period and to repeat the activation sequence with a frequency as a sequence n=1, 2 . . . N of activation sequences, while the frequency is sufficiently high to dissolve the pulse of the test person's circulation.

The assessment of the training state of an athlete, the measurability of his training progress and the establishment of the most effective and efficient training plan is a challenging task, the relevance of which also economically comes more and more into the focus of the approach to modern sports. A comprehensive data collection of the stress level of the active muscles under defined performance requirements and in training is required for obtaining objective assessment criteria that are indispensable for ensuring physical integrity and optimizing performance. Here it would be desirable if information about respiration (lung), blood transport (cardiovascular), and musculature (energy metabolism) could be provided.

For sports physiological performance assessment, mainly the methods of spiroergometry and lactate diagnostics are used today. In addition, pulse oximeters from the medical sector are frequently used to determine the pulse rate and arterial oxygen saturation ($SpO_2$). In the basic technology of pulse oximetry, it is common to record two wavelengths (typically 660 nm and 940 nm), which are produced by LEDs in rapid cycles and with an optical sensor. Due to the rapid cycles, the pulsatile pulse signal can be divided into a variable and a constant component. The variable component of the signal represents the pulsatile arterial blood.

By analysing the absorption ratios of the two wavelengths in the variable signal, the oxygen saturation of the arterial blood ($SpO_2$) can be calculated because at the wavelengths considered, the absorption coefficients for oxygenated and deoxygenated hemoglobin differ and behave in opposite directions.

Due to the transparency of the tissue in the observed spectral range, additional signals can be generated through changes in the strong and, above all, varying outgoing light. These influences are generally reduced each by a third measuring point without LED lighting.

This technology makes it possible to construct small and very fast sensor units that can be attached directly to the usual body parts (muscles).

The light source of pulse oximeters is preferably an integrated multi-spectral LED module which serves as a pulsed and controllable illumination unit. The LEDs are very fast switchable, variable light sources (typically 10-5000 µs). Without thermal problems, they work with a high light intensity which is uncritical for the tissue. Advanced pulse oximeters (e.g., Masimo CO pulse oximeters) also use multiple (up to 9) wavelengths in the VIS and NIR range for additional analysis of other hemoglobin derivatives, such as carboxyhemoglobin or methemoglobin. Such extended pulse oximeters work exclusively with wavelengths above 600 nm.

From US 2012/0253153 A1, a device with the features of the general term of claim 1 is known. The known device is a pulse oximeter, which is—similar to the previously described one—extended in its functionality to that effect that further substances can be analysed by the addition of additional wavelengths. However, the described device is not suitable for tissue or muscle oximetry (which will be described below), since the illumination unit has to be operated at a high clock frequency (sampling rate) which is necessary to detect the pulse rate, and at this high clock frequency, the course of intensity as a function of the distance to the lighting unit can not be detected with nearly sufficient resolution. However for muscle oximetry, the course of intensity as a function of the distance from the illumination unit is needed with high resolution.

In spiroergometry, various respiratory parameters are determined in order to obtain comprehensive qualitative information about the muscular, circulatory, and pulmonary system. The parameters to be determined are mainly the volume of oxygen inhaled per minute, the volume of carbon dioxide exhaled per minute, and the values and quantities derived therefrom. The most important parameters to be determined for training control are the VO2max and the ventilatory thresholds (VT1 and VT2), where VO2max is the maximum oxygen uptake of the athlete.

For the determination of these quantities, the wearing of a breathing mask by the test person is obligatory in spiroergometric measurements. In addition, spiroergometry usually takes place under defined ambient conditions in laboratories of performance centres. Due to the complexity of the devices, an outdoor enforcement is extremely expensive—technically and financially. Therefore, the data collection can only be performed at scheduled performance di-agnostic examination appointments and thus gives only a temporary picture of the training condition of the athlete.

In spiroergometric examinations, in addition to the determination of the test person's performance-related breathing parameters, the heart rate (pulse rate) is generally determined as well, which is also performance-dependent and recorded with another sensor system. This can be done conventionally via an ECG, a heart rate monitor, or a pulse oximeter.

To record physiological parameters outside of medical applications, various new approaches have been introduced in recent years to cover increasingly different physiological parameters.

In US 2015/0282724 A1, for example, a camera system is provided with which the pulse rate, the heart rate variability (HRV), and the respiratory rate (RR) are determined via the pulsatile changes from the image signal. This shows, that different optical sensor systems can be used to determine physiological parameters.

In US 2015/0282746 A1, a system is presented in which (with a conventional pulse oximeter with two wavelengths)

the respiration rate is also recognized and evaluated by the respiratory cycle via the blood shift in the body in addition to the pulse rate.

The fact that this is particularly well-suited in the field of sports with high signal intensities has been shown with this technology by the establishment of some clinical devices. A comparable original measurement and evaluation is also shown in WO 2014/139830 A1 in FIG. 7.

US 2015/297133 A1 shows a method, which determines the ventilatory threshold (VT) from a measured heart rate (HR) and a respiration rate (RR). It is proposed to determine the 2 parameters from two sensors, for example an ECG sensor and a respiration sensor. From this it can be seen that the determination of a ventilatory threshold (VT) is not only possible via spiroergometric methods but can also be realized by means of continuous mobile measurement methods without breathing gas measurement.

Trough combination of the information from the previous two applications, it can be clearly seen that the ventilatory threshold of an athlete can be determined by a single optical sensor.

The other method conventionally used in performance diagnostics is lactate threshold determination. This is generally done punctually and minimally invasive. The aerobic threshold is frequently set at 2 mmol/l (power at 2 mmol/l lactate concentration) and the anaerobic threshold at 4 mmol/l lactate concentration (power at 4 mmol/l lactate concentration). The anaerobic lactate threshold is in the range of 75-90% of maximum power for many athletes depending on their performance. The thresholds to be determined by means of lactate are dependent on further external parameters (e.g., selection of the load protocol, cadence, . . . ) and require a profound knowledge of the use of various threshold models.

In order to be able to determine this threshold continuously and non-invasively, it has been proposed to determine this via the pH value in the muscle. The optical determination of the pH value in the muscle was described in "Non-invasive determination of exercise-induced hydrogen ion threshold by direct optical measurement", Babs R. Soller et al., *J. Appl. Physiol* 104: 837-844, 2008", in WO 2011/091280 A2 and in "Validation of a spectroscopic sensor for continuous, noninvasive measurement of muscle oxygen saturation and pH", G. Ellerby et al., Physiol. Meas. 34 (2013) 859-871. The parameters muscle oxygenation, muscle pH value, and muscle lactate concentration can be determined from the same measured values. Devices and methods for determining muscle oxygenation have been disclosed for this purpose in US 2008/097173 A1 and in WO 2010/053617 A2. This shows, that muscle oxygenation and muscle lactate concentration can be converted directly into each other and that by measuring the oxygenation, the lactate value determination for performance diagnostics becomes obsolete.

A method for the non-invasive spectroscopic determination of the lactate value in the medical field of application in the spectral range 1000 nm to 1700 nm has been described in WO 2004/097365 A2. It also cites many scientific publications on this topic of non-invasive lactate value determination.

Other devices and methods for determining muscle oxygenation during exercise are described in WO 2010/093865 A1, WO 2013/158459 A1, US 2014/016132 A1, and US 2015/0196238 A1. All these systems are characterized by multispectral or spectroscopic devices in the NIR spectral range, which continue to detect with at least two distances between the illumination unit(s) (transmitter) and optical sensors (receiver) the optical signals and determine the physiological values. Among experts, these technologies are referred to as NIRS (Near Infrared Spectroscopy) methods or tissue or muscle oximetry. It should be noted in US 2015/01962381, that three detector units are to be integrated in the sensor unit for receiving the physiological signals.

In contrast to the pulse oximeters, which record the pulsatile signal components and thus determine the arterial oxygen saturation and the pulse rate, tissue oximeters are used to determine the oxygen saturation of the hemoglobin in the microcirculation. In microcirculation, oxygen is exchanged between blood and tissue cells. This is often referred to as tissue oxygen saturation.

The usual commercial tissue oximeters (NIRS systems) have a simple NIR photometric recording. As already described, this typically consists of one or more controllable multispectral LED illumination units and a plurality of photo sensors mounted at different distances. The distances between the transmitters and receivers are generally arranged in the range between 1 cm and 10 cm.

The use of several detectors (spatially resolved remission measurements) is based on the properties of the tissue as a scattering and absorbing medium. The spatially resolved measurement has the advantage that the signature of the light-absorbing components becomes stronger the greater the distance between the emitter and the detector is. As a result, the measurement is ensured with the greater distance, even if the signal quality is worse due to the falling intensity than for the short distance. The spatially resolved measurement therefore allows a certain separation of absorption and scattering.

In these devices, the support wavelengths must be switched sequentially and the different photo sensors are usually read sequentially. Due to the larger distances between the transmitter and the receiver, the signal intensities are often very low, so that it is necessary to work with comparatively long exposure times of the sensors. In addition, due to the relatively small differences in the absorption cross sections of the $O_2Hb$ and $HHb$ in the typically examined spectral range between 700 nm and 950 nm, a very good signal-to-noise ratio (SNR) of the measurement is necessary, which usually has a longer temporal smoothing demands. Thus, these sensors are not suitable for temporally resolving the pulsatile signals and therefore can not provide information such as the pulse rate or the arterial oxygen saturation ($SpO_2$).

Thus, the tissue oximeters are not suitable for detecting the parameters which are important in the overall assessment of the physiological signals of the human body of an athlete. The systems are not pulse resolved, that is, they can not record pulse rate, arterial oxygen delivery, pulse intensity, and respiratory rate. Thus, the first available mobile devices for determining the muscle oxygenation are often operated in parallel with other sensor systems, for example for detecting the pulse rate (PR). When using these devices, the coupling of different sensors for PR measurement is complex and thus no uniform analysis software can be offered and used. It can be considered as additional disadvantages, that the sensors absorb the signals from different locations on the body and that a precise synchronization of the measured data must additionally be carried out.

In order to obtain a more differentiated picture with pinpoint accuracy of a test person at the time of training, it is important to avoid the conventional methods described, such as place-bound and complex spiroergometry, punctual lactate diagnostics or the continuous and non-invasive method of NIRS with different sensor systems at different points of the body to use with different configurations, evaluation methods, and restrictions.

The systems presented so far are not suitable for the combined measurement of the parameters set out in a single, compact, mobile housing for a mobile application on the muscle of the athlete.

This is not feasible with the methods presented so far and corresponding to the state of the art, since on the one hand a high optical signal quality must be achieved, the signals must be generated in the same area of the tissue, and— especially for measuring the heart rate—high clock frequencies are required to determine the heart rate safely from the photoplethysmogram (also pleth curve—temporal course of the pulsating hemoglobin signal). This requirement is made even more difficult by movement artefacts of the active musculature, which superimpose the signals.

Simply linking a different technology or combining several known technologies does not create a satisfying solution.

It is therefore an object of the present invention to obviate the limitations and disadvantages of existing systems and, more particularly, to create a device and method that can determine different physiological parameters of the athlete's lung, heart, and muscles, including pulse oximetry and muscle oximetry, with a very compact device that—without restricting the athlete's training operation—continuously records data by directly being attached to the body surface.

These and other objects are achieved according to the invention by a device having the features of patent claim 1 and a method having the features of patent claim 15.

According to the invention, a camera sensor is provided to be available as a CCD or CMOS camera frame sensor with a 2-dimensional array of sensor elements. The camera sensor is arranged to the lighting unit in such way that it can be applied on the skin on the same side of the body part as the lighting unit and adjacent to it to capture the light which passes by transflection through the body of the test person from the lighting unit to the camera sensor.

The data processing unit is set up to read out the camera sensor in each activation sequence at the activation start times $t_k$ (k=1, 2 ... M) and over the respective activation period, and combines the detected intensities of the sensor elements of subregions of sensor elements and the respective activation sequence from the sequence n=1, 2 ... N of activation sequences and the respective activation starting time $t_k$ (k=1, 2 ... M) assigned to record as time series. The assignment of a sequence number of the activation sequence and the respective start times within each activation sequence are identical in content to an absolute time specification for each activation in each activation sequence since they can be converted into one another: the activation time $t_k$ in the n-th activation sequence is assigned the following time τ since the beginning of the measurement: $\tau(n,t_k)=n\cdot T_s+t_k$, where $T_s$ is the duration of an activation sequence, and it is assumed that the activation sequences follow one another without interruption.

In doing so, the data processing device is set up to combine the intensities of the sensor elements in subareas of the camera sensor by reading out lines of the camera sensor which lie parallel to the connection axis between the illumination unit and the camera sensor. Since there are a plurality of such lines, along which the distance from the illumination unit to the respective sensor element of the line of the camera sensor increases, this represents a large number (equal to the number of lines) of time-parallel measurements along the line direction. Such temporally parallel lines can be combined into a single averaged line, with the intensities then having a significantly improved signal-to-noise ratio in the averaged line. Such averaged numbers can be formed for single or all wavelengths. By means of the averaged lines, it is possible on the one hand to work with a clock frequency of the activation sequences which is sufficiently high to dissolve the pulse signal of the blood circulation. On the other hand, by averaging over many lines of the camera sensor, a sufficiently good signal-to-noise ratio can be achieved, so that the intensity curves in the NIR wavelength range can be evaluated in relation to each other and as a function of the distance from the illumination unit, despite the high clock frequency, for muscle oximetry. In the state of the art of tissue oximetry, high exposure times were used to achieve sufficient signal-to-noise ratios, which precluded the resolution of the pulse signal of the circuit.

The illumination unit has at least one LED type with emission maximum <590 nm, preferably with an emission maximum at 575 nm, where the absorption coefficients for oxygenated and deoxygenated hemoglobin differ significantly. This allows an additional check as to whether a periodic signal supposedly recognized as a pulse signal actually involves the pulse signal of the circuit, since the real pulse signal is accompanied by a corresponding pulse signal for oxygenated hemoglobin. Thus, the pulse signal of the circuit can be reliably distinguished from other periodic or approximately periodic signals (for example, breathing or periodic motion while running).

In a preferred embodiment, it is provided that the data processing unit is set up to read respectively the lines of the camera sensor, which run parallel to the connecting line between the illumination unit and the camera sensor, and to average all lines to form an average line intensity progression $$\bar{I}(i)_{\lambda m} = \frac{1}{N_Z} \sum_{a=0}^{N_Z} I_a(i)_{\lambda m}$$

where i=1, 2 ... $N_{Sp}$ the continuous column index and $N_{Sp}$ the number of columns of the camera sensor, and the index λm symbolizes the wavelength of the emission maximum of the respective LED type and as averaged intensity $\bar{I}(i)_{\lambda m}$ (n, $t_k$) of the respective activation sequence n from the sequence n=1, 2 ... N of activation sequences and the respective activation start time $t_k$ (k=1, 2 ... M) are recorded as time series. Typical camera sensors have several hundred lines, so that averaging over all lines results in a very good signal-to-noise ratio. The averaging over all lines corresponds to the summation of the intensity values of all sensor elements of each column to an intensity value averaged for each column.

Furthermore, it is preferred that the data processing unit is set up to combine the intensities of the sensor elements over all rows and columns to form a camera sensor intensity $$\bar{I}_{\lambda m} = \frac{1}{N_Z \cdot N_{Sp}} \sum_{a=0}^{N_Z} \sum_{i=0}^{N_{Sp}} I_a(i)_{\lambda m}$$

integrated via the sensor, where i=1, 2 ... $N_{Sp}$ symbolises the continuous column index, $N_{Sp}$ the number of columns of the camera sensor, a the continuous line index, $N_Z$ the number of lines of the camera sensor, and the index λm the wavelength of the emission maximum of the respective LED type, and to record these of the respective activation sequence n from the sequence n=1, 2 . . . N of activation sequences and the respective activation start time $t_k$ (k=1, 2 . . . M) as time series $\bar{I}_{\lambda m}(n,t_k)$ of the camera sensor intensity. For each emission maximum, a time series $\bar{I}_{\lambda m}(n,t_k)$ is thus available which can be evaluated individually or in combination.

In a preferred embodiment, it is provided that the data processing unit is set up to summarize and record the time series $\bar{I}_{\lambda m}(n,t_k)$ of the camera sensor intensity of the different wavelengths $\lambda 1$, $\lambda 2$ . . . $\lambda L$ to a wavelength-spanning individual time series $\bar{I}(n,t_k)$ of the camera sensor intensity.

It is further preferred that the illumination unit comprises at least one LED type with emission maximum in the range of 500 nm to 540 nm and an LED type with emission maximum in the range of 570 nm to 585 nm. In particular, an LED type with a wavelength of about 525 nm and an LED type with a wavelength of 575 nm may be present. These wavelengths allow good discrimination between oxygenated and deoxygenated hemoglobin since 525 nm is an isosbestic point, that is the absorption of oxygenated and deoxygenated hemoglobin is the same. In contrast, the absorption of deoxygenated hemoglobin at 575 nm is significantly smaller than that of oxygenated hemoglobin.

In a preferred embodiment, it is provided that the illumination unit comprises at least three different LED types whose emission maxima span an NIR wavelength range from 650 nm to 920 nm. Evaluations of tissue oximetry and muscle oxygenation can be performed in this wavelength range.

Preferably, the illumination unit has at least four different LED types with emission maxima distributed in the spanned NIR wavelength range.

In a preferred embodiment, it is provided that the illumination unit in the NIR wavelength range has a plurality of LED types with emission maxima distributed in the wavelength range 800-1100 nm, including an LED type with emission maximum at 960 nm, an LED type with emission maximum at 930 nm and at least two LED types with emissivity maxima in the range of 790-920 nm, and that the data processing unit is adapted to measure from the absorbance at 960 nm the concentration of water, taking into account the absorption through fat at 930 nm and the absorption by hemoglobin by evaluating at least two absorptions at interpolation points in the range 790-920 nm, preferably with at least two supporting points in the range 800-910 nm.

In a preferred embodiment, it is provided that the data processing unit is set up to subject the time series of the wavelength-spanning camera sensor intensity $\bar{I}(n,t_k)$ a Fourier transformation and to seek a distribution peak at a fundamental frequency, which is accompanied by one or more distribution peaks of harmonics at multiples of the fundamental frequency, for detecting the pulse signal.

In this context, it is preferred that the data processing unit is set up to confirm the correctness of the detection after detection of a pulse signal, if in the signal of the camera sensor intensity $\bar{I}_{\lambda m}(n,t_k)$ with $\lambda m$ from the wavelength range of 570-585 nm a stronger, pulsating signal with the fundamental frequency than in the signal of the camera sensor intensity $\bar{I}_{\lambda m}(n,t_k)$ with $\lambda m$ from the wavelength range of 500-540 nm can be found. As explained above, the absorption of oxygenated hemoglobin in the wavelength range 570-585 nm is significantly greater than that of deoxygenated hemoglobin, so that the pulse signal in the wavelength range 570-585 nm is clearer.

In this case, it is further preferred that the data processing unit is set up to apply a dynamic band pass filter for pulse signal detection in the Fourier spectrum of the wavelength-overlapping camera sensor intensity, wherein the centre of the accepted frequency band is at the known fundamental frequency and the width of the frequency band is predetermined, wherein the dynamic band pass filter follows changes of the detected fundamental frequency of the pulse signal if the changed fundamental frequency is within the accepted frequency band and wherein a hypothetically newly detected pulse signal with its fundamental frequency is discarded, if it is outside the accepted frequency band. This test is based on the fact that the pulse rate does not change abruptly, so that when the pulse frequency is changed to an actually changing pulse frequency of the test person to the dynamic bandpass filter, the change follows and only the supposedly detected pulse signal is discarded, where a too large and sudden change of the supposedly new pulse signal compared to the last detected one occurs.

In a preferred embodiment, it is provided that the data processing unit is set up to apply in the Fourier spectrum for respiratory signals a dynamic band pass filter, where the centre of the frequency band is at the detected respiratory frequency and the width of the frequency band is predefined, where the dynamic band pass filter follows changes in the detected respiratory, if the changed respiratory frequency is within the accepted frequency band and where a hypothetical newly detected respiratory signal with its new respiratory frequency is discarded, if this frequency is outside of the accepted frequency band.

In a preferred embodiment, it is provided that the data processing unit is set up to evaluate the time series $\bar{I}_{\lambda m}(n, t_k)$ of the camera sensor intensity for emission maxima $\lambda m$ in the NIR wavelength range in relation to each other and their dependencies on the distance from the lighting unit (given by the column index i=1, 2 . . . $N_{Sp}$, i.e. the distance increases with increasing column index i) to hence evaluate the degree of oxygenation of the muscle.

In order to explain the principles of the present invention, the scientific basics of tissue spectroscopy, the physiological measurement technology and the specific properties of actual accessible optoelectronic system components must be discussed in greater detail. It is known that the light on its way through the tissue is decreased either by scattering or by absorption. Since the scattering in the tissue is relatively constant in the conventional spectral range of the NIRS, it makes sense to consider such additional spectral ranges in which the absorptions, especially of the hemoglobin, are considerably higher. If the proportion of absorption relative to scattering is higher, then the pulsatile portions—especially those of the hemoglobin—are stronger for detecting hemoglobin changes by heartbeat or respiration. This is given in the visual spectral range (VIS), just between 500 nm and 600 nm. A further advantage of the stronger absorption cross-sections is that the radiation does not penetrate so deeply into the tissue, and thus the optical signals originate only from the directly finely structured tissue and in general no larger vessels are detected in the measurement volume. Since the larger vessels are more altered during muscle contraction than the direct muscle tissue characterized by microcirculation, weaker motion artifacts are to be expected by this effect. Another advantage of using this spectral range is the significant spectral characteristics of oxygenated and deoxygenated hemoglobin ($O_2$Hb and HHb). Thus, in this area with high signal intensities, specifically the pulsation of the oxygenated and deoxygenated hemoglobin can be examined.

The theoretical basis for the spectroscopic or photometric investigations is the Beer-Lambert law. With this, concentrations of absorbing molecules in solutions can be determined by the passage of light $$I_\lambda = I_{0,\lambda} e^{-\mu_{a,\lambda} \cdot l_\lambda} \quad (1)$$

With $I_\lambda$ the light intensity after passing through the substance to be examined, $I_{0,\lambda}$ the irradiated light intensity, $\mu_{a,\lambda}$ the wavelength-dependent ($\lambda$) total absorption coefficient and the path length l through the substance. Due to the scattering properties of tissue, an effective path length is generally to be expected, which is generally also wavelength-dependent, which, however, can be neglected in this spectral range (500-1000 nm) and application. Alternatively, an additional wavelength-dependent scattering coefficient can be used.

Transformation results in the absorption $$A_\lambda = \ln\left(\frac{I_\lambda}{I_{0,\lambda}}\right) = -l_\lambda \cdot \mu_{a,\lambda} \quad (2)$$

This general law now needs to be further diversified, since a substance such as human blood or human muscle tissue consists of many chemical sub-entities (molecular compounds) and their absorption coefficients differ depending on the wavelength. With the substances one receives $$\mu_{a,\lambda} = \Sigma_{i=1}^n \varepsilon_{1,\lambda} \cdot c_i \quad (3)$$

For m wavelengths this can now be transformed with the assumption that the path lengths remain the same for all wavelengths, as follows:

$$\begin{bmatrix} \ln\left(\frac{I_{\lambda 1}}{I_{0,\lambda 1}}\right) \\ \vdots \\ \ln\left(\frac{I_{\lambda m}}{I_{0,\lambda m}}\right) \end{bmatrix} = -l \begin{bmatrix} \varepsilon_{1,\lambda 1} & \cdots & \varepsilon_{n,\lambda 1} \\ \vdots & \ddots & \vdots \\ \varepsilon_{1,\lambda m} & \cdots & \varepsilon_{n,\lambda m} \end{bmatrix} \begin{bmatrix} c_1 \\ \vdots \\ c_n \end{bmatrix} \quad (4)$$

The individual extinctions, which are described by the matrix $[\varepsilon_{n,\lambda m}]$ together give the total absorption matrix $E_\lambda$. Thus, this relationship can be written in the following form:

$$A_\lambda = -lE_\lambda C \quad (5)$$

Or $$C = -\frac{1}{l} E_\lambda^{-1} A_\lambda \quad (6)$$

This makes it possible to determine the concentrations of the substances with known extinction coefficients $E_\lambda$, the measured intensity $I_\lambda$ and the known irradiated light intensity $I_{0,\lambda}$.

For the physiological diagnosis of an athlete, oxygenated and deoxygenated hemoglobin are important, but also the influences of melanin (skin colour, water and fat (subcutaneous fat layer)) have to be considered.

When measuring the hemoglobin concentrations in the tissue, it must furthermore be noted that the heart beat pulse propagates through the arteries with a high proportion of oxygenated hemoglobin (HbO 2, typically 98%). Thus, the pulse is characterized not only by a general change in the hemoglobin content in the muscle but also specifically by the (systolic) increase in oxygenated hemoglobin. In contrast, hemoglobin's relative changes in concentration caused by movement, respiratory, and muscle tensions differ in that their concentrations shift equally.

Thus, by using wavelengths in which the hemoglobin has isosbestic absorption coefficients (e.g., about 520 nm) and wavelengths where the $O_2Hb$ has significantly higher extinction coefficients than the HHb, mathematically an accurate differentiation can be made. The typical wavelength here is 575 nm.

Another advantage is that the pulse signal can be detected more stably, since the average difference of the signal between pulse maximum and pulse minimum in the visible spectral range in relation to the fundamental signal in the range 575 nm is significantly higher than in the VNIR spectral range. This difference can be greater than a factor of up to 5.

However, the use of these wavelengths for pulse-resolved analysis fundamentally contradicts the requirements of conventional NIRS systems. Thus, conventional NIRS systems with lower absorption coefficients usually have to work with longer path lengths in the tissue. Furthermore, NIRS technology generally requires the acquisition of multiple spectral bases, but with lower frequency and with higher precision.

Since the additional pulse monitoring has hitherto been achieved only by the use of different sensor systems at different measuring points in the tissue, a new solution is proposed here.

In camera technology, highly integrated miniaturized digital CMOS camera sensors have become established. These sensors are mostly used with an imaging optics for the generation of two-dimensional images. These CMOS image sensors with the capability of continuous fast imaging for digital video systems are state of the art and find versatile application e.g. in mobile multifunction devices (smartphones), automation technology, quality control, medical technology, and microscopy.

These camera sensors have 0.5-5 million structured light receivers. Furthermore, adjustable amplifier circuits, digitizing elements (A/D converter), dark pixels, and other advantageous functions are also integrated miniaturized in these sensors. Furthermore, with CMOS sensors of the newer generations, an internal black balance can follow. At the edges, pixels are covered in black. These are additionally read out and used internally for black level normalization. Although this does not solve the problem of extraneous light influences, but the usual problems, such as the drift of the sensor signals in case of temperature fluctuations or fluctuations in the supply electronics. This allows images to be taken with very short exposure times and high light intensities. As a result, extraneous light effects are generally low. If extraneous light influences occur, a background image without LED illumination and with a greatly reduced ROI (region of interest) can additionally be recorded in order to additionally optimize the image acquisition.

The CMOS sensors are very compact with typical image edge sides of 3-10 mm and require little space for additional electronics, which would be necessary when using conventional photo detectors. By further integrated logic, these components can be extensively parameterized. In the case of very special parameterization, such pixel arrays or CMOS camera sensors can be used very advantageously for a sensor system described here. Another advantage when using sensor arrays and, in particular, CMOS sensor arrays is their high availability. Two-dimensional sensor arrays in particular also allow a higher measuring speed with simultaneously better signal-to-noise ratios. The digital data can be transmitted very quickly—sequentially or in parallel—to a processor, whereby many commercial processors are already directly equipped for operation with digital CMOS camera arrays.

The very good image quality and the low light requirement of these sensors (high quantum efficiency at typically over 50%) allow the use of small, miniaturized lighting units.

Such a sensor array typically allows 0.5-5 million pixels to be captured with one exposure of an LED. Each individual pixel contains intensity information in typically 10, 12, 14, or 16 bit data depth. Since this very high number of pixels is not required for this application, the amount of data can be greatly reduced by using different functions of the sensor and by selecting a partial area of, for example, approximately 500×50 pixels. This is made possible by using the field capturing possibility of the camera sensors to speed up the recording. For CMOS sensors, regions of interest (ROI) can be set which make it possible to read out only the set, interesting image area of the sensor while maintaining the basic data rate. Furthermore, through the method of binning (summarizing pixels) or skipping (skipping pixels), the resolution can be further reduced.

These digital optical data can then be transmitted to a processor and further integrated there with approximately 50 distance-dependent intensity values with a very good signal-to-noise ratio.

Due to the reduced amount of data, the sensor can be operated at a higher frame rate. In this way, typically up to 200 to 500 images per second can be generated. The high image frequency can be used to record the time-varied optical signal, changed through the pulse, with a high sampling rate. Attention must be paid to compliance with the Nyquist-Shannon sampling theorem, whereby a time signal must be sampled with at least twice the highest occurring frequency. Since a maximum pulse of an athlete with 200 beats/min, that is about 3 per second is to be assumed, the sampling theorem is satisfied with the recording principle of the invention and beyond, a very good pulse-resolved detection with very high data depth is possible.

For example, a typical camera sensor may include 1280× 960 sensor elements, which is 960 parallel lines with a length of 1280 sensor elements each. The lines run parallel to the connecting line between the illumination unit and the camera sensor. At full resolution, that is detection of all sensor elements, the frame rate is limited to 45 fps (frames per second). With a limited image size of 1280×100 sensor elements (that is only 100 lines lying one on top of the other, forming a centre stripe on the camera sensor surface while maintaining full resolution in the line direction), a frame rate of 346 fps can be achieved. The reading out of at least 100 lines is preferred.

The good temporal resolution is required to determine the pulse-based parameters such as the heart rate HR, the pulse strength PI or the respiratory rate RR from the recorded intensity curve. Especially motion artifacts are characterized by short-term (higher-frequency) signal components. Therefore, a sufficiently high sampling rate is helpful to be able to separate these artifacts from the primary signal (pulse curve).

When considering the camera sensors, the spectral sensitivities must also be taken into account. Very important here are just the visual (VIS, about 400 nm to 650 nm) and near infrared (NIR, about 650 nm to 1200 nm). The NIR spectral region is the optical window of the human body, that is the area in which optical radiation can penetrate deeper into the tissue. The measurement in the VIS range, in turn, does not allow large penetration depths, but is characterized by strong pulsation, since the hemoglobin absorbs very strongly here. Many available camera sensors (CMOS or CCD) are sensitive especially in these spectral ranges.

According to the invention, the two-dimensional sensor arrays are not used to perform a spatially resolved image acquisition in two dimensions, which is the most common application of 2D arrays of sensor elements. Rather, the sensor elements are used in a sensor direction for detecting the distance-dependent signals in order to determine the light intensity as a function of the path length through the tissue (spatially resolved remission measurement). The other dimension serves to integrate the signals of the individual photocells to improve the signal-to-noise ratio. Thus, a sequential integration of the optical signals with successive exposure times into a parallel integration with only one light pulse per defined wavelength and also only a passage of light through the tissue can be realized.

The method enables the use of adjacent columns to produce more photo signals with one exposure per time unit and thus to obtain optimized signals. This is made possible in particular by the very homogeneous littering properties of the tissue. Parallel measurement here means a quasi-simultaneous measurement. Of course, it is clear that the individual pixels and lines of the sensor are read out sequentially. However, the sampling frequency is so high (typically >40 MHz pixel clock rate) that it is possible to speak of a quasi-synchronous measurement of the parallel lines, in particular since the exposure of the photo receivers virtually occurs at the same time. This achieves the reading of sub-images at higher speeds. Better signal-to-noise ratios can thus be generated in the optical data acquisition.

Thanks to this arrangement, the illumination system (e.g. a miniaturized, multispectral LED illumination unit) and the optical receiver system can be integrated directly in the sensor at a measuring point. The illumination and the camera sensor can be attached directly to the measuring area on the muscle. This makes it possible to dispense with relatively rigid and large optical devices for transmitting the light. Furthermore, the lighting is much higher in this way. This in turn increases the luminous efficacy, so that the exposure times can be kept very short and the proportion of measuring light is very high despite possible extraneous light.

The whole arrangement thus contains only a multispectral LED-based illumination unit and the highly integrated CMOS sensor array. Thus, the optical module can be made very small (preferably less than 10 mm×20 mm×5 mm, typically about 10 mm×10 mm×1.5 mm).

In addition to the optical module, the sensor must contain another processor module. This processor module can either be integrated with the optical module or can be designed separately from the optical module via a thin cable. It is of great advantage if the optical sensors can be placed very small and directly on the muscle. This allows the athlete to record the physiological data during exercise without any restrictions on the training process.

It is also possible to introduce the optical sensor module directly into a textile of the athlete, so that the sensor does not have to be attached separately to the muscle.

Such a device can therefore also be equipped with radio-based data transmission (for example Bluetooth, WIFI or ANT+) and an integrated power supply (rechargeable battery or battery) and can be attached directly to the muscle of the athlete. On glass fibres or other optical transmission elements (lenses, etc.) can be dispensed with. Due to the types of CMOS arrangements of a few millimetres, these have sufficient space in a miniature system.

Preferably, the device has a housing and is designed as a compact unit so that it can be placed well on a muscle of the athlete and so even during exercise has no disturbing influence on the training process. The compact unit contains at least the multispectral light source and the sensor array, a processor for data evaluation and storage, an electrical supply unit and a device for wired or wireless data transmission.

But it is also possible to integrate the optical unit consisting of multispectral LED and CMOS sensor array separately in a housing. The arithmetic evaluation can then take place in an evaluation device separated from the device.

If in the device—according to the invention—the measured values are digitized and transferred via an electrical connection to a central evaluation unit, the transmission cables can be kept thin. At the same time, it is not necessary to design the sensor or the device—according to the invention—so large on account of necessary computers, input or output devices, that attachment to the measuring locations is no longer possible. An external evaluation device also offers the possibility of temporary data storage or data evaluation by means of more complex, mathematical methods.

With the present invention, a comprehensive physiological picture of the athlete's response to muscular stress can be generated from purely optical measurements and evaluations. For use in performance diagnostics (e.g. oxygen saturation in muscle tissue), light is preferably present in the visible (VIS) and near-infrared (NIR) spectral range, in particular in the very near infrared range, e.g. in the VNIR range of 500 nm to 1000 nm. This light is preferably generated by the described integrated multispectral LED illumination module.

Physiological blood and tissue values are within the scope of the present description all values, that can be determined in an athlete for performance diagnostic purposes or to monitor the training process. This applies in particular to the parameters already established below.

The parameters that can be directly determined with the device and method are, for example:
  Heart rate (HR)
  Pulse shape and structure
  Heart rate variability (HRV)
  PI (Pulse or Perfusion index)
  Respiration rate (RR)
  Muscle oxygen saturation ($SmO_2$)
  Tissue hemoglobin index (THI)
  Concentration of deoxygenated Hb in tissue (cHHb)
  Concentration of oxygenated Hb in tissue ($cO_2Hb$)
  Concentration of $H_2O$ ($cH_2O$)
  Arterial oxygen saturation ($SpO_2$)

For the further considerations, it is helpful to differentiate between the temporal pulse-based and the spectral absorption-based parameters in the parameters. The pulse-based (pulsatile) parameters are calculated from the time-variable pulse curve (plethysmogram). These include the parameters HR, HRV, PI, RR, and the pulse shape and structure. The absorption-based measured values are calculated from the different intensity and absorption ratios at the spectral interpolation points. These include the parameters $SmO_2$, THI, cHHb, $cO_2Hb$, and $cH_2O$.

The time-dependent evaluation makes it possible to distinguish between information from the tissue and arterial blood.

For the determination of the arterial oxygen supply, the calculation of the percentage $SpO_2$ concentration as in "The light-tissue interaction of pulse oximetry" (Mannheimer Ph.D., Anesth., Analg., 2007, December; 105 (6 Suppl): S10-7) can be performed. In the evaluation, comparable to the conventional oximetry, two spectral ranges can be compared. The conventional wavelengths of 660 nm and 910 nm can be used for this, but the pulsatile multispectral approach can also be used and additional NIR wavelengths can be deployed for the evaluation.

The calculation of the parameters from the optical signals can be carried out directly in the integrated processor of the sensor system.

As explained in the description, some of the parameters that are determined today by performance diagnostics can be calculated and derived from these measured values with different mathematical methods. Thus, with the present invention, today's conventional performance diagnostic tests can be replaced or supplemented by a single sensor system which, in contrast to current methods, is non-invasive, continuously measuring, and can be used by the athlete during normal exercise without significant restrictions.

The image sensor can preferably be integrated monolithically in a semiconductor component together with the evaluation device and possibly a control device and optionally a memory device for reference data, so that a compact and cost-effective design is possible and expensive additional wiring can be omitted or can be kept even lower.

It is important to note that not only can a single measuring device be positioned at a fixed body site, but it is also possible to acquire data in parallel at different measuring points by using a plurality of measuring devices. Thus, mismatches between e.g. the right and left side of the body (e.g., cycling, to determine the degree of fatigue of both legs) can be examined. A common purpose is to place one sensor on the stressed musculature and another sensor centrally on the chest or shoulder to study oxygenation differences and temporal distribution patterns. Another frequently required combination is the comparison of the measured values between muscle and brain by a muscle-forehead circuit.

Figure 2:
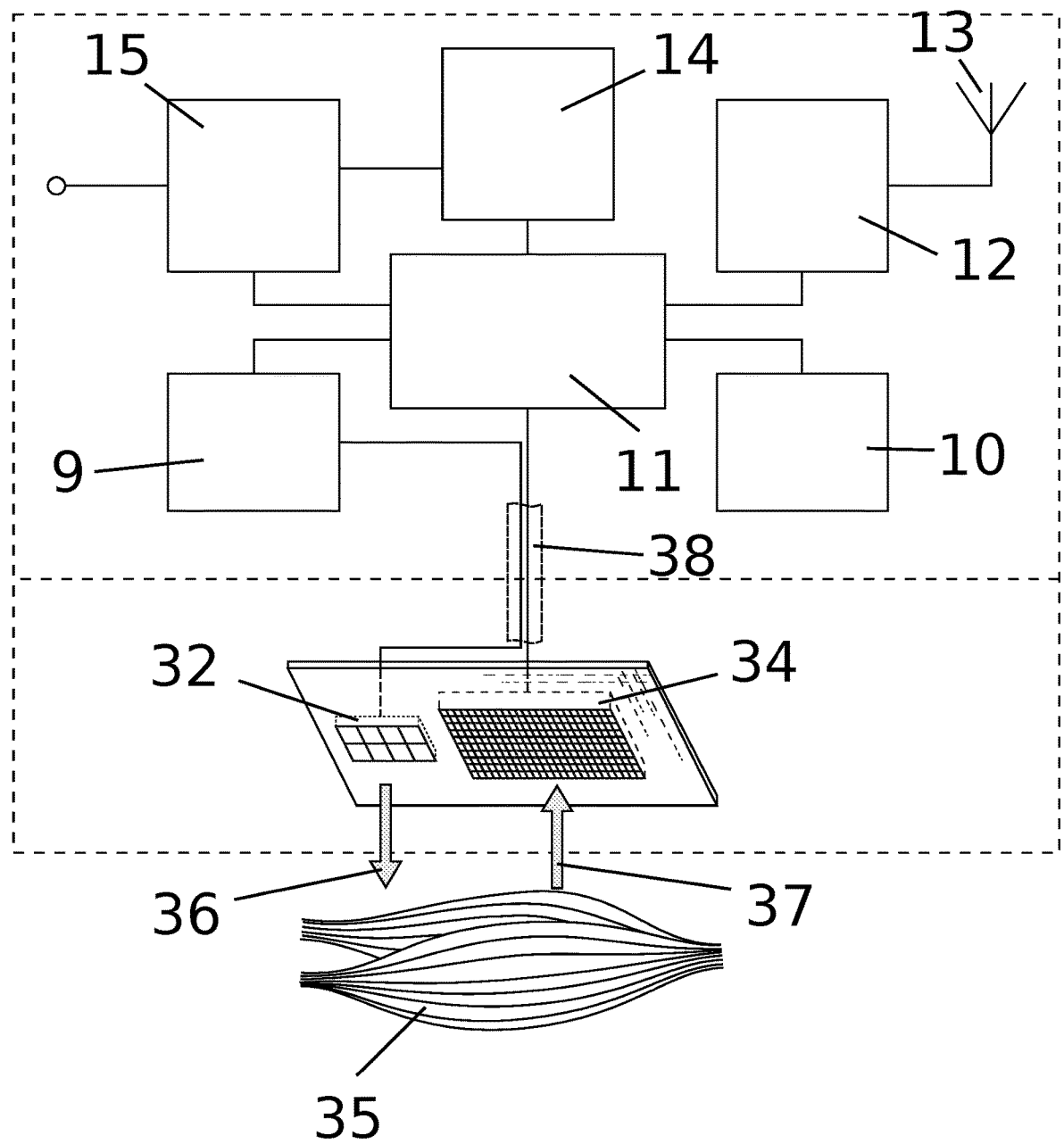
Figure 3:
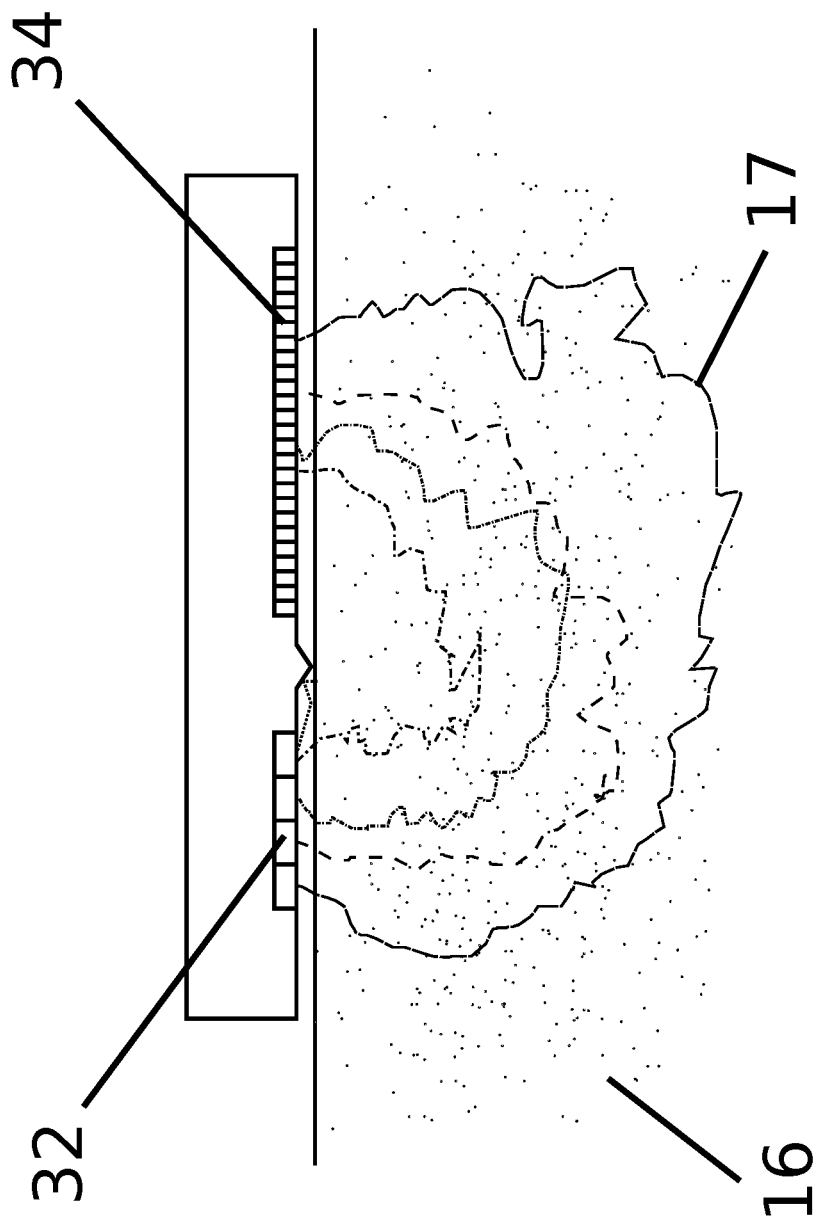
Figure 4:
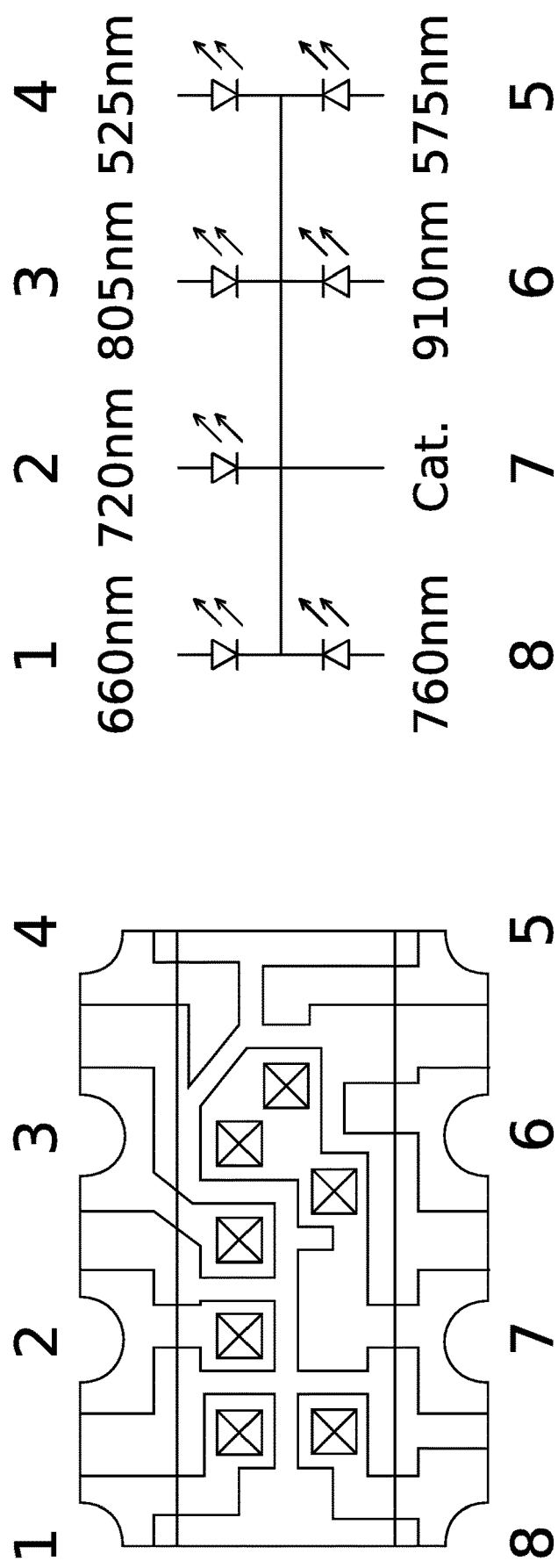
Figure 6:
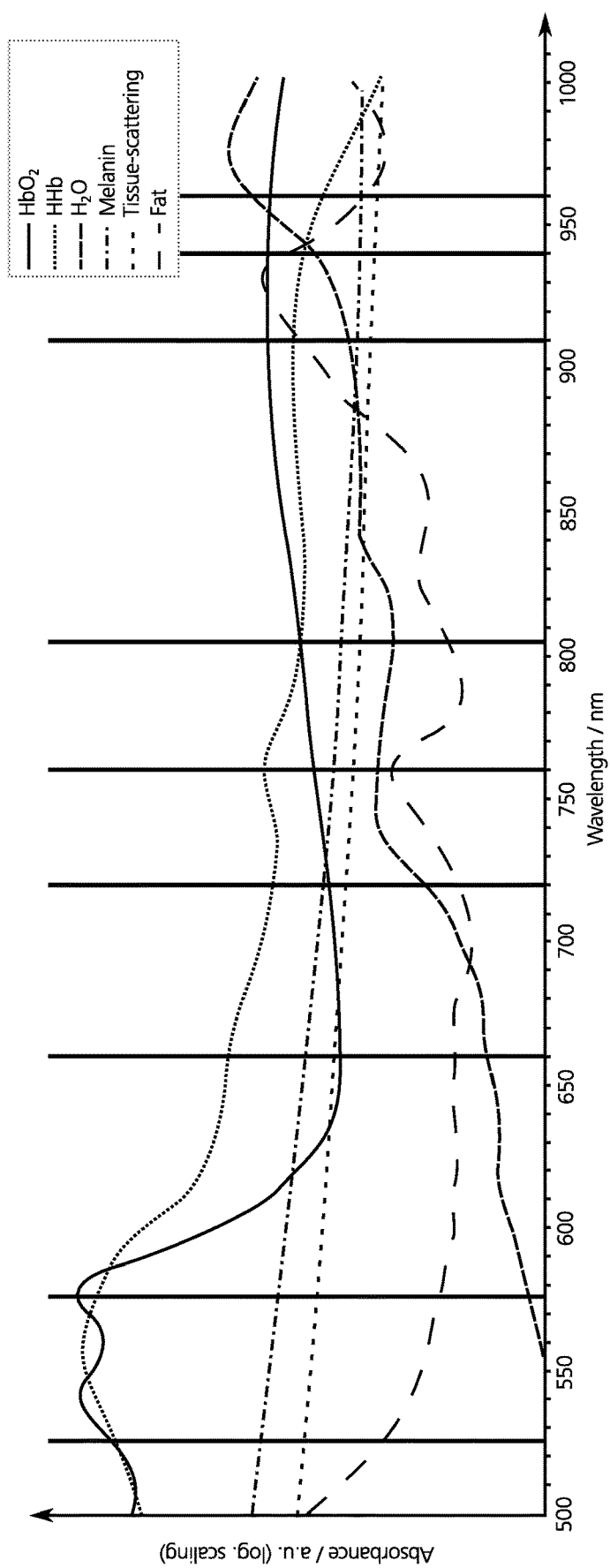
Figure 7:
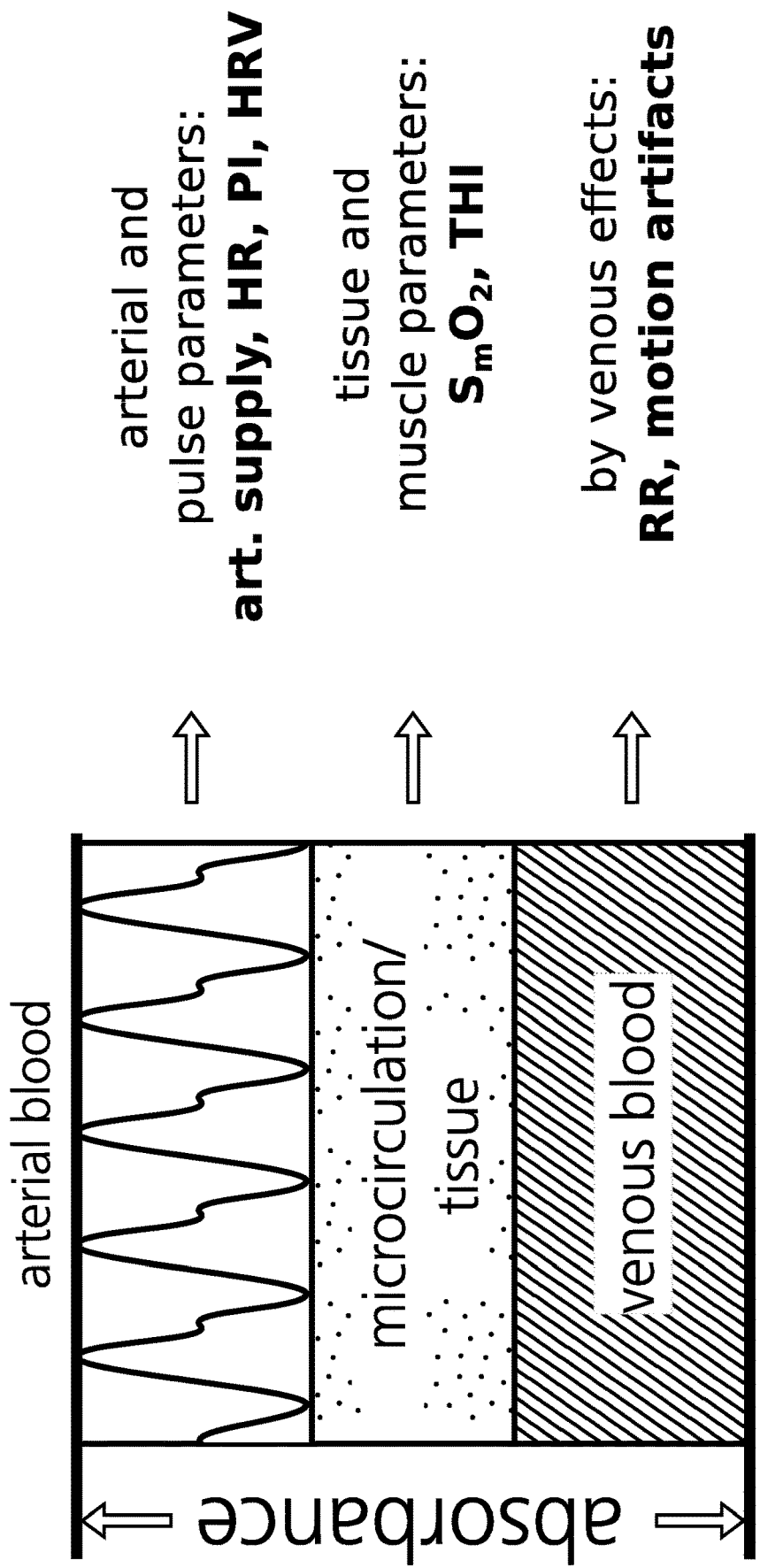
Figure 8:
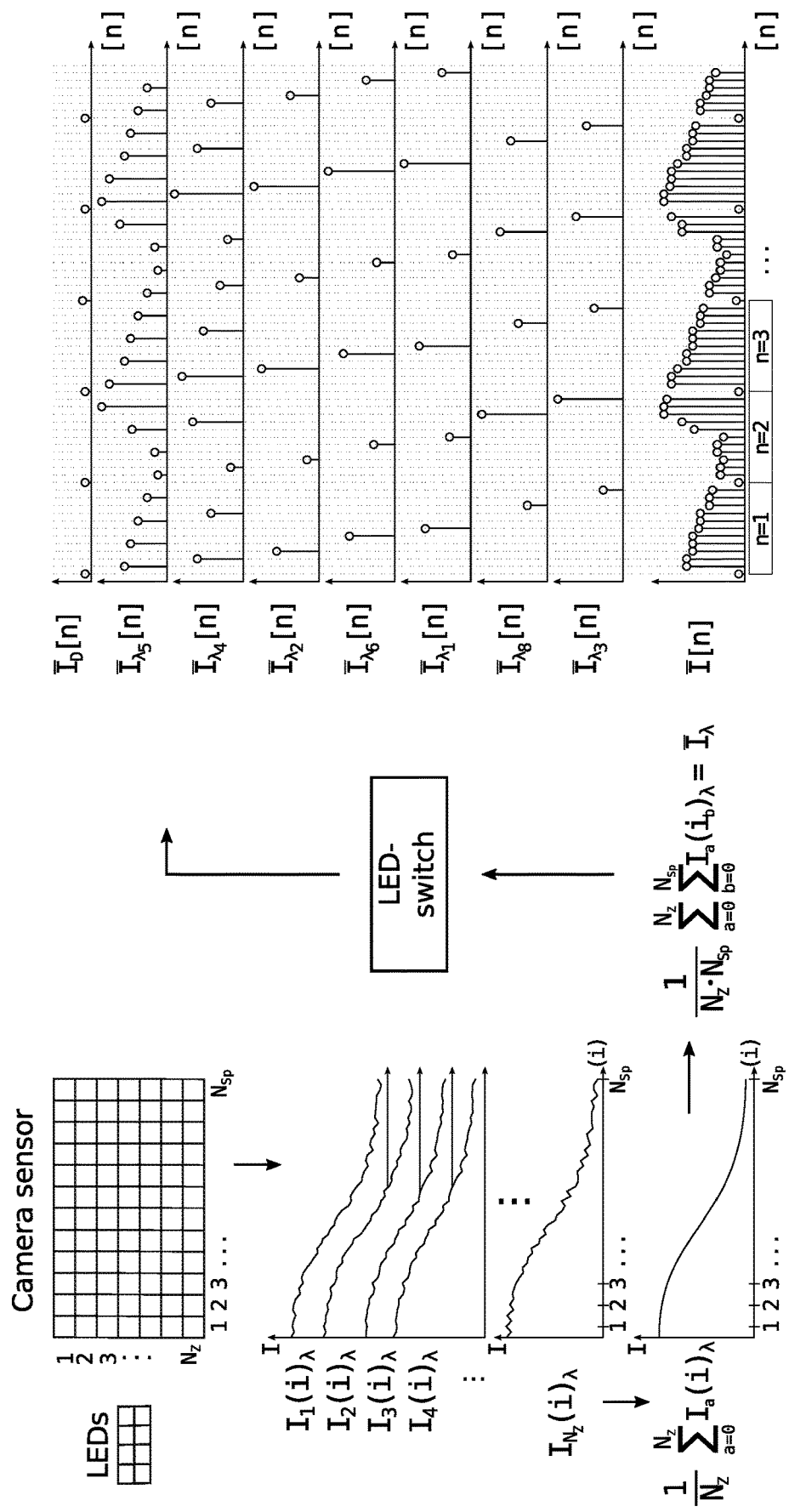
Figure 9:
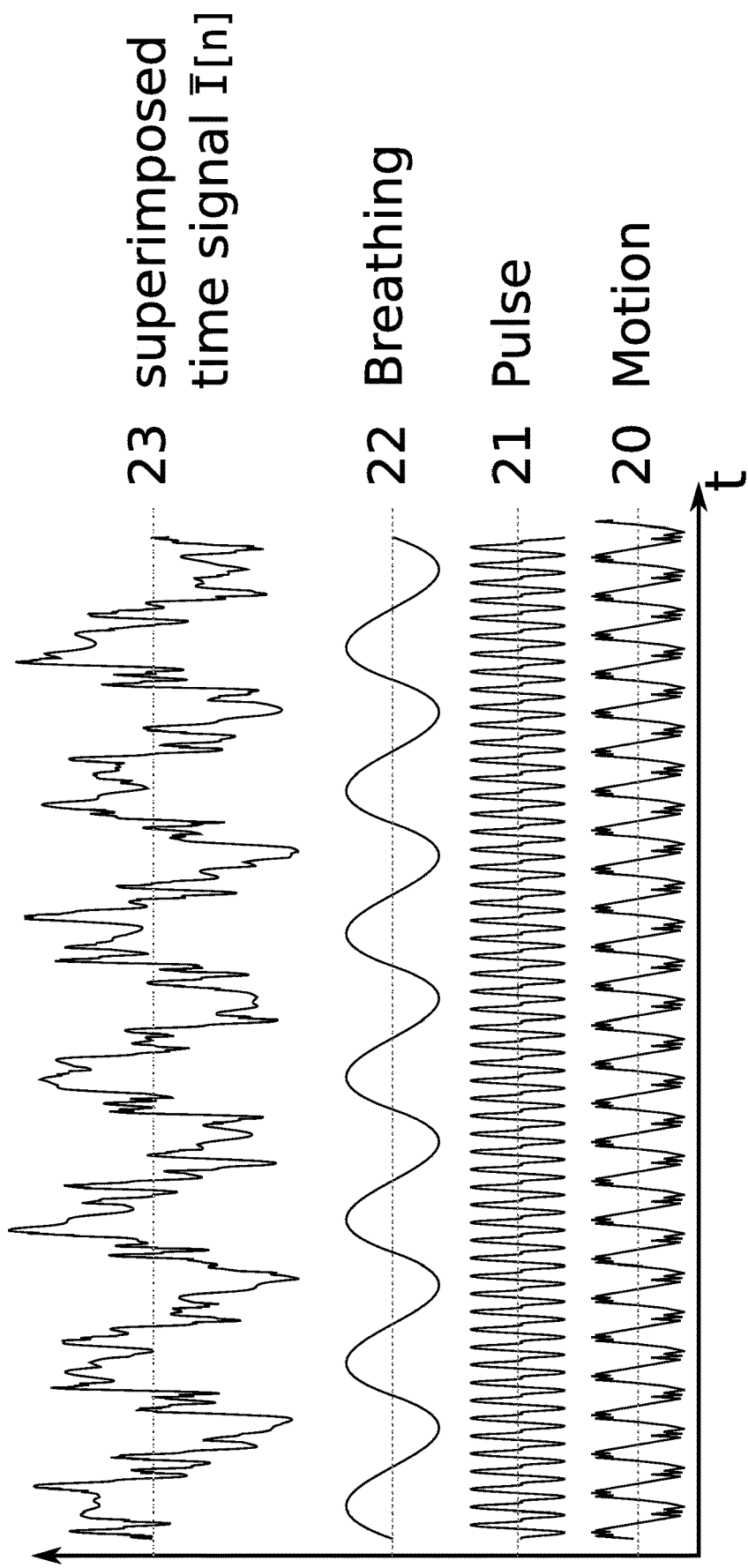
Figure 10:
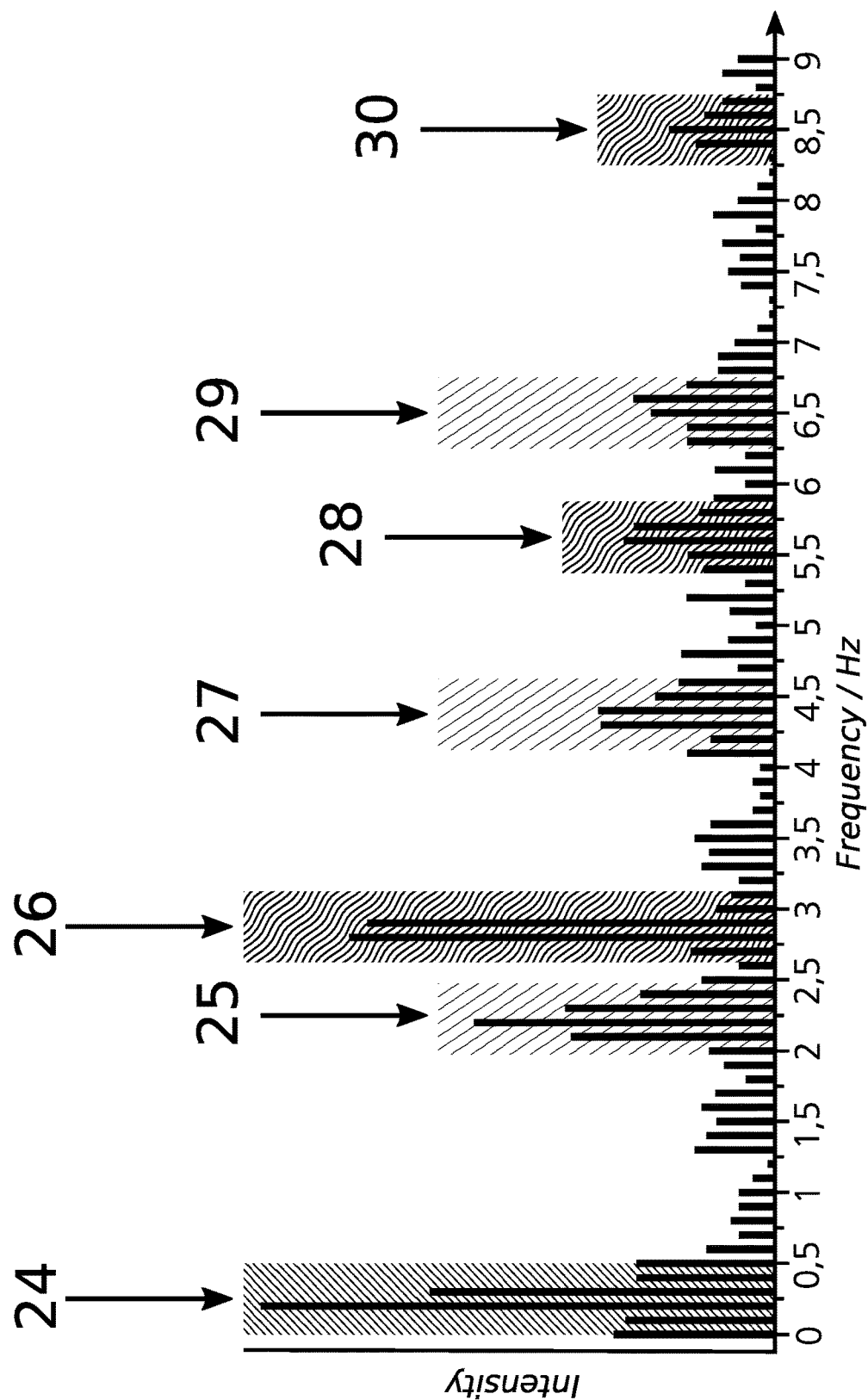

The invention is explained in more detail below with reference to exemplary embodiments in the drawings, in which FIG. 1 is a schematic perspective view of the device according to the invention from a point of view within the observed body region, FIG. 2 is a block diagram showing the structure and operation of the apparatus, FIG. 3 shows a schematic sectional view through a device according to the invention and through the tissue underlying the device of the examined body site of the test person, FIG. 4 shows a plan view of a preferred compact, multispectral LED module with seven individually controllable LED semiconductors and a corresponding position matrix with the emission maxima of the LED types used, FIG. 5 a) shows an integrated module, in which the optical unit with the electronic unit is integrated in a housing and arranged and attached as a whole unit on the skin at the observable body part of the test person, FIG. 5 b) shows an embodiment of the device with an optical sensor module which is mounted directly on the skin and connected to a digital data processing unit via a cable to the optical sensor module and which can be placed at another location, FIG. 6 shows VIS/NIR absorption spectra of the muscle-relevant substances for spectroscopic assessment, namely oxygenated hemoglobin ($O_2Hb$), deoxygenated hemoglobin (HHb), water ($H_2O$), melanin, fat, and tissue scattering with significant wavelengths marked, which are well suited for a data recording, FIG. 7 shows schematically constant and pulsatile fractions of body components which contribute to the absorption, FIG. 8 shows a schematic plan view of a lighting unit and a camera sensor as well as read-out intensity signals and their summary, FIG. 9 shows the wavelength-overlapping camera sensor intensity signal $\bar{I}(\tau)$ as a function of time as well as the components contributing thereto, resulting from respiration, pulse, and movement of the test person, FIG. 10 shows the Fourier spectrum of the wavelength-overlapping camera sensor intensity signal with distribution peaks contained therein, which originate from the pulse, respiration, and movement of the test person, FIG. 1 shows a schematic diagram of the structure of a device according to the invention. The body surface on which the device is mounted is stated at 31. Below this, the relevant measuring medium or tissue 33 is located, which may be, for example, the muscle that is mainly stressed during training, but in principle also any other body location, such as the breast, shoulder, or forehead. The use on the wrist can also be interesting, whereby the integration of the measuring device into a so-called "wearable" (for example fitness tracker or smart watch) is also conceivable.

The multispectral illumination unit 32 with a matrix of LEDs sequentially emits light pulses with emission maxima at different wavelengths into the tissue in a defined time sequence (activation sequence), wherein the incident light is immediately scattered there after entry and homogenized in the propagation direction. As it passes through the tissue, the light is also absorbed by the substances, contained in the tissue, with fixed known extinction coefficients.

The light comes out at different points of the tissue again. The area in which the CMOS optical camera sensor 34 is placed is important. There, the light is measured as a function of the distance from the point of irradiation and recorded as an analogue signal. By this arrangement, in which the illumination unit 32 and the camera sensor 34 lie in one level, the light is measured in the so-called transflection, since the light partly passes through the tissue (transmission), but also partly is diffusely scattered or reflected (reflection).

This signal is amplified directly in the camera sensor 34, digitized and transmitted in parallel or serially for each pixel to a processor unit.

The camera sensor 34 is preferably a high-resolution, two-dimensional CMOS digital camera sensor array. The array must be a so-called monochrome sensor, that is a sensor without a structured colour filter matrix. Thus, the sensor can receive light radiation of different wavelengths, depending on its specific sensitivity curve.

FIG. 2 shows a block diagram of a preferred embodiment of the device. In the device, a data processing unit (arithmetic unit) 11 takes over the entire control, data synchronization, data readout, and buffering. Firstly, the data processing unit assumes the parameterization of the camera sensor 34 (parameterization here means the setting of the registers of the camera sensor such as gain, skipping, binning, exposure time, ROI, pixel rate, etc.), the digital data acquisition of the camera sensor 34, and the control of the multispectral illumination unit 32. Furthermore, the data processing unit can optionally also perform a data reduction, data buffering or data preprocessing.

The multispectral illumination unit 32 emits light 36 onto the measurement area 35 of the muscle. This light exits the muscle in a distance-dependent manner as analysis light 37 as described above and strikes the CMOS camera sensor 34.

The camera sensor 34 is a two-dimensional CMOS digital camera sensor. In one direction (connecting axis of LED illumination unit 32 and camera sensor 34—this direction is referred to in the present application as the row direction), the distance dependence of the exiting light is detected due to the growing distances to the entry point into the muscle.

The sensor is already amplifying and digitizing the photoelectric signals. These are then transmitted via a connecting line 38 in parallel or serially to the data process.

The intensity adaptation between the illumination unit and the sensitivity of the camera sensor is to be controlled particularly favourable over the length of the switch-on time of the LEDs of the illumination unit. Thus, a very precise constant current source 9 can keep the light intensity from one light pulse to the next very stable, but the intensity can be set very precisely in small steps.

With the help of a rechargeable battery 14, the sensor module can be operated during training without a fixed supply connection.

Optionally, during the acquisition process the current data may be communicated to other devices via a digital radio link 12 with an antenna 13 (incorporated into the housing). Another possibility is the transmission of data during training, but especially after the completion of data acquisition by wire via an output unit 15 to other devices. This cable can be used simultaneously to power and charge the battery 14.

In a memory 10, the recorded physiological parameter values can be buffered.

On other devices the data can be further processed and evaluated, but above all they can be displayed and stored in a larger context.

FIG. 3 shows the optical arrangement in a section through the device and the underlying muscle. Thus, light 17 enters the tissue 16 from the respectively controlled monochrome LED of the multispectral LED illumination unit 32 and is many times diffusely scattered and—on its way through the tissue—absorbed, depending on the substance concentrations and the wavelength. Because this is a random process, the light is scattered and reflected in all directions in an equally distributed manner. However, individual light paths, which also impinge on the camera sensor, have only been drawn by way of example. As described, this principle is called transflection.

FIG. 4 shows a preferred embodiment of the multispectral LED illumination unit with seven separate wavelengths; more specifically, the LEDs have seven separate emission maxima, with the half-widths of the emission spectra being about 15 nm. The size of the module is typically 4.9 mm×3.2 mm×1.2 mm (length×width×height). The seven different dyes are arranged together on a carrier so that they can be controlled and switched separately via a common cathode. The spectral assignment of the LED is shown in the following table, whereby the predominant function of the measuring signal at the wavelength for the physiological evaluation is indicated shorthand.

| | | |
|---|---|---|
| 520 nm | Strongly pulsatile, but almost isosbestic | Pos 4 |
| 575 nm | For strongly pulsating $O_2Hb$ band | Pos 5 |
| 660 nm | For pulse oximetry and $SmO_2$ | Pos 1 |
| 720 nm | $SmO_2$ | Pos 2 |
| 760 nm | $SmO_2$, significant band in the HHb signal | Pos 8 |
| 805 nm | $SmO_2$, isosbestic point | Pos 3 |
| 910 nm | Pulse oximetry and $SmO_2$ | Pos 6 |

The LED 4 (520 nm) is used to differentiate the pulsatile components as a function of the oxygen saturation. At 575 nm (LED 5), the high absorption coefficient of $O_2Hb$ determines the signal through the oxygenated hemoglobin, while at 520 nm, the absorption coefficients of $O_2Hb$ and HHb are very similar (isosbestic). Thus, in an analytical comparison, the two signals can distinguish between the delivery of highly oxygenated blood in the arteries and desaturated blood to the microcirculation and veins, respectively.

The five wavelengths in the NIR range (1, 2, 8, 3, 6) are mainly used for data generation for NIRS technology, that is the determination of muscle oxygenation. For this purpose, a somewhat lower sampling frequency is sufficient since no higher-frequency signals (in particular pulsatile signal components) must be detected.

Since the Pleth curve is known via the evaluation of the pulsations in the VIS spectral range (LEDs 5 and 4), the arterial oxygen saturation ($SpO_2$) can be determined in conjunction with the signals of LED 1 and LED 6, using the conventional pulse oximetry technology.

The assignment of the wavelengths of the illumination unit to the pulse-based and the absorption-based parameters makes it possible to operate the individual LEDs with different clock frequencies. This is achieved by defining an activation sequence of the LEDs. A preferred embodiment of an LED activation sequence is:

D,5,4,2,5,6,1,5,4,8,5,3

D stands for image acquisition without activation of an LED (dark image). Other criteria for the sequence are, that LED 5 is placed equidistantly in the sequence, that LED 4 may only follow LED 5 (which does not imply that 5 must follow the 4) and the pulse oximetry detection LEDs Signals (6,1) are directly consecutive. The LEDs for evaluating the NIRS signals and the dark image are distributed to fill the sequence, as they are integrated over a longer time range.

For the realization of the pulse resolution, the wavelengths intended for this purpose must be activated with the highest individual frequency since, as explained, the motion artifacts and the pulse must be sampled at a higher frequency.

The effective frame rates thus result from the camera frame rate $f_s$ and the occurrence in the sequence:

$f_{D,1,2,3,6,8}=1/12 \cdot f_s$, for the LEDs 1, 2, 3, 6, 8 as well as for the dark image D, $f_4=1/6 \cdot f_s$, for LED 4 and $f_5=1/3 \cdot f_s$, for LED 5.

If, for example, a frame rate of 300 fps (frames per second) is assumed, the individual LED frequencies $f_{D,1,2,3,6,8}$ result in each case at 25 Hz, $f_4$ at 50 Hz, and $f_5$ at 100 Hz.

FIG. 5 a) shows a possible embodiment in which the measuring device illustrated as a block diagram in FIG. 2 is completely integrated in a compact housing 18. The housing is shaped so that it can be comfortably attached to the body surface over a larger human muscle and can also be integrated into possible fastening systems which hold the device stably on the surface of the muscle (1) even under heavy muscle stress. It is advantageous, if the housing is formed in the manner that it is protected against moisture (sweat, water). FIG. 5 b) shows a further embodiment in which the optical unit of the device is kept very small and can also be attached directly to the muscle at the measuring point. The advanced unit for data processing, communication, and power supply is housed in a second compact housing 19, which is connected via a thin cable to the optical sensor unit. Thus, for example, the optical sensor unit can be firmly integrated into a garment and the second housing for data exchange, power supply, and other functions can be arranged separately next to the actual device for measuring value acquisition.

FIG. 6 shows the individual spectra of pure, oxygenated hemoglobin, deoxygenated hemoglobin, water, the skin pigment melanin, fat, and the typical scattering properties of human tissue. The plot of absorption in the Y-axis is logarithmic. The presentation should mainly show the typical curves of the absorption curves and the characteristic absorption bands. Since the concentrations of the individual chemical components in the muscle can vary greatly and unknown substances contribute in addition to the spectra, in practice a combined evaluation with as many spectral bases as possible by means of absorption spectra makes sense. For this purpose, a multivariate statistical analysis method is used to determine the contributions of the single substances to the recorded spectra, and in particular to determine the relative contribution of oxygenated hemoglobin to deoxygenated hemoglobin (oxygenation), the tissue hemoglobin concentration, and concentrations of the other substances, especially of water. Illustratively, in such an analysis method, the measured spectrum is represented as a linear combination of the individual spectra of the pure substances, and the coefficients of the individual spectra are determined in that linear combination of the individual spectra, which provides the best match with the measured spectrum. For example, when determining the concentration of water, the pronounced absorption of water at 960 nm is used. Since at this wavelength, as can be seen from FIG. 6, absorption by fat and by hemoglobin also occurs, their proportions must be taken into account in the multivariate statistical analysis method. For this, the absorption at 930 nm is used, where fat has a high absorption, and several support points in the wavelength range 800-910 nm, which are characteristic of the contributions of oxygenated and deoxygenated hemoglobin. In the combined statistical evaluation of the absorptions at all wavelengths, therefore, the contributions of the individual substances can be determined, in this example in particular the water.

With the embodiment described above in connection with FIG. 4 with an LED illumination unit with LEDs at positions 1-6 with emission maxima as indicated in the table reproduced above, an evaluation and detection of the water concentration is not possible. If evaluation is also desired in relation to water, at least two more LEDs must be provided: one having an emission maximum in the range of 930 nm to be sensitive to the absorption of fat and an emission maximum in the range of 960 nm to be sensitive to the strong absorption of water there.

FIG. 7 schematically shows the proportions of the measured absorption of hemoglobin when measured in the muscle. The measured optical signal has a constant component and a pulsatile component.

The pulsatile component is generated by the pumping of the arterial blood by the heart. The strength of absorption in arterial blood is not equal at systole and diastole. This allows a differentiation. In a heartbeat, highly oxygenated blood is pumped into the measured part of the body. Here, the oxygen saturation of hemoglobin in a healthy man lies in the range of 95% to 99%. The pulsating signal component is wavelength-dependent and depends on the measuring point and the detected spectral range. From this pulsating signal, for example, the heart rate (HR), the heart rate variability (HRV), and the pulsation index (PI) could be determined as parameters.

The tissue-derived signal is divided into two parts. One part depends on the constituents of the tissue, the other part depends on the scattering properties of the tissue, which influence the real light paths. From the range of the substances' contents, the muscle oxygenation, the tissue hemoglobin index, but principally also the fat and glucose portion (energy supply) can be calculated. The scattering properties of the tissue can be detected via the distance-dependent evaluation on the CMOS sensor array.

On the one hand, the respiratory rate, on the other hand, the movements of the athlete can be detected by the shift of the venous blood portion. During a breathing cycle, a larger amount of blood is shifted from the central area of the body to the peripheral areas and back again.

FIG. 8 schematically shows the generation of the various signals for the calculation of the different parameters. For the individual images of the camera, the spatial dimensions $N_{Sp}$ is evaluated as a number of columns and $N_Z$ as a number of lines, the row direction (with the column number i as a running variable), running parallel to the connection axis of the LED illumination unit and the camera sensor, and the column direction orthogonal thereto. In the first step, the individual lines, whose intensity decreases with increasing number of columns i and thus increasing distance from the light source, are averaged together. The result averaged over all rows represents an intensity function in the row direction i, with i=1, 2 ... $N_{Sp}$:

$$\bar{I}(i)_{\lambda m} = \frac{1}{N_Z}\sum_{a=0}^{N_Z} I_a(i)_{\lambda m}$$

Since the wavelength is different for each image within the activation sequence, the index λm is carried along. Since there is an activation start time for each activation within the activation sequence, the average intensity $\bar{I}(i)_{\lambda m}$ also represents a time series as a function of the time r given below. The individual activation phases within the activation sequence are each assigned an activation start time $t_k$ with k=1, 2, ... M (with M as the number of activation phases within a sequence) and an illumination duration, wherein it must be noted that the illumination duration varies per LED type individually but of course always must be smaller than the time period between two consecutive start times $t_{k-1}$ and $t_k$.

The time duration $T_A$ between the individual activation start times is predetermined by the camera frame rate $f_A$ so that the activation start times of the LEDs are arranged equidistant from each other—but the switch-off times may be individually different:

$$T_A = \frac{1}{f_A} = t_k - t_{k-1} = \text{const.}$$

The time duration $T_S$ between two start times of successive activation sequences in turn results from the time $T_A$ between the individual activation start times within the activation sequence and the number M of activations of the activation sequence, it being assumed that the activation sequences are repeated continuously without pause:

$$T_S = \frac{1}{f_S} = M \cdot T_A = M \cdot (t_k - t_{k-1}) = \text{const.}$$

The individual times at which the same LED is switched on give the signal $\bar{I}_{\lambda m}[n,t_k]$ as a time series with λm as the index for the emission maxima of the LED types D,1,2,4, 5,6,8, where D is not an LED type in the true sense, but represents the absence of illumination (dark phase). Instead of the sequence number n of the activation sequence and the activation start time $t_k$ within the activation sequence, the absolute time $\tau(n,t_k)$ of the respective activation start time can also be indicated $\tau(n,t_k)=n\cdot T_s+t_k$. The corresponding signals (e.g., $\bar{I}[\tau]$ and $\bar{I}[n]$) may therefore be considered equivalent.

The averaged intensity distributions $\bar{I}(i)_{\lambda m}$ of the different wavelengths partially already serve as input data for the calculation of the spectral absorption-based parameters (e.g., $SmO_2$). To obtain the pulsatile (pulse-based) parameters, the mean intensity distribution $\bar{I}(i)_{\lambda m}$ is averaged over the columns i. Thus, the intensity distribution $\bar{I}(i)_{\lambda m}$ becomes an intensity value $\bar{I}_{\lambda m}$, wherein each of these intensity values a time $\tau(n,t_k)=n\cdot T_s+t_k$ is assigned to, according to the respective activation, which is not listed in the following formula:

$$\bar{I}_{\lambda m} = \frac{1}{N_{Sp}}\sum_{i=0}^{N_{Sp}} \bar{I}(i)_\lambda = \frac{1}{N_Z \cdot N_{Sp}}\sum_{a=0}^{N_Z}\sum_{i=0}^{N_{Sp}} I_a(i)_{\lambda m}$$

In fact, for each wavelength λm, this is a time series $\bar{I}_{\lambda m}(\tau)$, as shown on the right side in FIG. 8.

If the LED is connected in the already described activation sequence D,5,4,2,5,6,1,5,4,8,5,3, first, the eight time series $\bar{I}_D(\tau)$, $\bar{I}_5(\tau)$, $\bar{I}_4(\tau)$, ... $\bar{I}_3(\tau)$, result, which are shown among another. These can also be combined into a time series $\bar{I}[\tau]$, as shown at the bottom right in FIG. 8.

The respective signals $\bar{I}(i)_{\lambda m}$, $\bar{I}(i)_{\lambda m}[\tau]$, and $\bar{I}[\tau]$ can be used separately in the evaluation, but also in combination with each other.

In the present invention, this combination is used to allow the evaluation of the individual parameters even during intensive exercise, which is also characterized by strong regularity.

FIG. 9 shows the components contributing to the signal $\bar{I}[n]$. The periodic signal (20) produced by muscle contraction and vibration (movement) will cause a shift of the hemoglobin in the muscle tissue. The pulsatile signal (21), caused by the heartbeat, will affect mainly the oxygenated arterial blood as already shown and is additionally characterized by its distinctive shape by diastole, systole, and dichrotic notch (by aortic valve closure) of the cardiac cycle. The frequency (22) caused by the respiration is characterized by a shift mainly of the venous part (high HHb part). The respiration rate can be assumed to be always lower than the pulse rate, especially when using the athletic performance examination.

The following properties, which are used by the present invention in order to enable as precise a separation as possible, apply to the three influences shown: pulse, respiration, and (muscle) movement.

1. The pulse signal is indicated by:
   1.1. A characteristic shape caused by systole and diastole of the heart as well as the closure of the aortic valve and the flexible nature of the arteries, and through Fourier transformation has a specific frequency spectrum with multiple harmonic waves,
   1.2. An oxygenation increase per pulse, as the signal is caused by arterial pulse wave (arterial saturation $SpO_2$ typically at 98%), 1.3. Gradients/rate changes in a defined time range (heart rate variability) are physiologically limited.
2. The respiratory signal is indicated by:
   2.1. An almost sinusoidal course,
   2.2. A lower frequency than the pulse signal,
   2.3. Because the signal is caused by a mainly venous blood shift:
      2.3.1. No oxygenation increase per pulse,
      2.3.2. In the NIR range relative signal change, since the ratio of constant (veins/microcirculation) to variable proportion (arteries) changes due to increased penetration depth.
   2.4. Rate gradients (respiratory rate variability) are physiologically limited.
3. The motion signal is indicated by:
   3.1. A periodic but not sinusoidal waveform with many (disordered/undefined) harmonics,
   3.2. Because the signal is mainly caused by venous/microcircular blood shift:
   3.3. No oxygenation increase per pulse
      3.3.1. In the NIR range relative signal change, since the ratio of constant (veins/microcirculation) to variable proportion (arteries) changes due to increased penetration depth.
   3.4 Movement patterns can be determined for different sports and extracted by appropriate filtering (e.g., wavelet analysis with special wavelets) and predictive models (e.g., autoregressive moving average).

With this knowledge and the embodiment of the invention (selection and arrangement of the LED wavelengths, use of a fast 2D camera sensor), all physiological parameters of interest can be determined: those related to the pulse and those related to the respiration, as well as those related to the oxygenation of the tissue. Thereby, all of the test person's physiological parameters of interest can be detected with a single sensor device, which can also be made so compact that it can be attached to a location of the test person's body without obstructing the person's exercise. In the prior state of the art, different sensors or measuring devices were necessary for the different areas (pulse, respiration, oxygenation of the muscles), which then had to be attached to different locations of the test person's body. With the present invention, with a single compact optical sensor, the entire physiological parameter set can be detected without obstruction of the exercise.

The described characteristics of the signals pulse, respiration, and movement can be evaluated as follows. The numbering of the properties is included below and used for better representation.
1. Determination of the Pulse Signal:
   1.1. Characteristic Form of the Pulse Wave:
   In each pulse cycle, highly oxygenated blood is supplied to the vascular system, which can not drain immediately due to the resistance of the smaller vessels. This creates a maximum in the blood pressure curve that corresponds to the systolic blood pressure. The conclusion of the aortic valve causes an incision in the blood pressure curve. The blood pressure falls due to the flow of blood to the periphery, and falls to the next heartbeat to a minimum, the so-called diastolic blood pressure. The course of the blood pressure curve, which is composed of systole, incisor, and diastole, is "low pass filtered", as the distance from the heart increases and the characteristic dicrotic pulse wave is created by the flexibility of the vessels.

This characteristic of the pulse wave can be used to allow the determination of the pulse frequency by analysing the time course $\bar{I}[n]$. Since the pulse wave is not sinusoidal, through transformation of the time signal into the frequency domain (by Fourier transformation), in addition to the fundamental frequency other upper frequencies result, which are formed as integer multiples of the fundamental frequency. This is given in FIG. 10 for the distribution peak 25, which corresponds to the fundamental frequency of the pulse and to which harmonics 27 (at twice the frequency) and 29 (at three times the fundamental frequency) are identifiable. Thus, the pulse signal can be delimited from the respiration in the frequency domain as well, since this is similar to a sine and occurs without or with hardly pronounced harmonics. This is the case in FIG. 10 for the distribution tip 24, which can therefore be associated with respiration.

1.2. Oxygenation Increase Per Pulse:
   To test the oxygenation changes per pulse, the signals $\bar{I}_{\lambda_5}[n]$ and $\bar{I}_{\lambda_4}[n]$ are evaluated. The signal $\bar{I}_{\lambda_4}[n]$ at 525 nm serves as a reference, since it scans an isosbestic point whose intensity does not depend on the oxygenation. Using the signal at 575 nm $\bar{I}_{\lambda_5}[n]$, which is characterized by a large absorption distance between oxygenated and deoxygenated hemoglobin, allows the oxygen saturation to be evaluated for each individual pulse, thus providing a separation between signals of the pulse and due to movement.

1.3. Limited Change of the Pulse Rate:
   In addition, due to physiological limits of heart rate variability, the pulse wave can be filtered by a matched dynamic filter (band pass filter in the frequency domain) with the heart rate as the (dynamic) centre frequency and the allowed variability as the bandwidth, such that the respiration or movement are not included, provided that the corresponding rates (or frequencies) do not run into the defined frequency window here. This will never be the case for the respiration rate, since the pulse signal always has a much higher frequency than the respiration signal. The separation of the arterial pulse signal and the movement is achieved in this case by the examination of the oxygenation.

2. Detection of Respiration:
   2.1, 2.2 and 2.4: Sinusoidal, Lower Frequency than the Pulse and Limited Change in the Respiration Rate:
   The principle of the dynamic filter can also be applied to the signal of breathing. Here, a frequency spectrum is expected that has only a significant peak, since the signal of the breathing is sinusoidal-like and has no or hardly pronounced harmonics (property 2.1), which is the case in the frequency spectrum in FIG. 10 for the distribution peak 24. The filter can be parameterized on the assumption that the respiration rate is significantly lower than the pulse rate (property 2.2) and the variability of the respiration rate within a defined time window is clearly limited (property 2.4).

2.3. By Venous Blood Shift:
   2.3.1. Low Oxygenation Per Pulse:
   By evaluating the oxygenation with the signals $\bar{I}_{\lambda_4}[n]$ and $\bar{I}_{\lambda_5}[n]$, a delineation of the (arterial) pulse signal and the respiratory signal can be achieved. As a result, a decision can be made as to whether a found frequency can be assigned to the respiration or the pulse.

2.3.2. Relative Signal Change in the NIR Range:
   It should also be noted that the venous shift results in a change of the signal in the NIR range, since in the NIR range, relatively higher signal fluctuations are generated than in the VIS range. This is caused because higher penetration depths into the tissue are achieved in the NIR range and thus the proportion of venous or microcircular signals changes with respect to the arterial signals.

3. Movement:

Although the motion signal contains no information from which the physiological performance parameters are calculated directly, it must be decided for a found significant frequency, whether this was the pulse, the respiration, or caused by the movement. The examination of the motion signals is therefore to secure the pulse and respiration detection and the exclusion of rhythmic movements. This can be achieved again by examining the oxygenation (property 3.2.1) and changing the signal components in the NIR range (property 3.2.2).

In addition to the determination of oxygenation, the characteristics of the time course during exercise can be used to separate the motion signals. The signals that are generated by the contraction of the muscle or the vibration of the measuring device are characterized by a periodicity, which may differ depending on the performed sport (property 3.1). For example, a stronger influence of shocks is expected for carrying out a running training than for bike training. The different exercises produce specific waveforms, which may require the use of adapted analysis forms, e.g. enable wavelet analysis. The motion pattern can be stored as a wavelet and the signal can be examined. The wavelet can be considered as a special band pass filter, whose shift in the frequency domain produces a maximum where the frequency of the motion occurs.

FIG. 10 shows the frequency spectrum that can be generated from the discrete time signal Ĩ[n]. The respiration 24 is characterized by a single peak, the pulse is described by the fundamental frequency 25 and the harmonics 27 and 29. The signal of the movement has the fundamental wave 26 and harmonics 28 and 30. It can be seen, that the examination of the pulse rate by the query of the harmonics is not necessarily sufficient to decide whether one of the fundamental frequencies 25 and 26 is about pulse or movement. For this, the query of the oxygenation can be carried out.

The invention claimed is:

1. Device for the continuous and non-invasive determination of physiological parameters of a test person during exercise comprising
   an LED-based illumination unit, designed to be able to rest on the skin of the test person at a desired measuring point, with a plurality of different, juxtaposed LED types, whose emission maxima at different wavelengths λ1, λ2 ... λL lie from visible to NIR-wavelength range, wherein the lighting unit comprises at least one LED type with an emission maximum below 590 nm,
   a photo sensor, which is designed to rest on the skin of the test person in order to capture light emitted by the illumination unit and passing through the body of the person to an exit location in the area of the photo sensor,
   a data processing unit, which is connected to the photo sensor to read it out, and which is connected to the lighting unit and is adapted to operate the different LED types individually in a predetermined activation sequence at successive activation start times $t_k$ (k=1, 2 ... M) for a respective predetermined activation period to activate and repeat the activation sequence with a clock frequency as a result n=1, 2 ... N of activation sequences, the clock frequency is sufficiently high to resolve the pulse of the test person's circulation, wherein
   a camera sensor, based on CCD or CMOS with a two-dimensional array with rows and columns of sensor elements is used as the photo sensor,
   the camera sensor is arranged relative to the lighting unit so that it can rest on the skin on the same side of the body part as the lighting unit and adjacent to it to detect light passing by transflection through the body of the test person to the camera sensor,
   the data processing unit is set up to read out the camera sensor in each activation sequence at the activation start times $t_k$ (k=1, 2 ... M) and over the respective activation period, and to record the detected intensities of the sensor elements, combined over subregions of sensor elements and the respective activation sequence from the sequence n=1, 2 ... N of activation sequences and the respective activation start time $t_k$ (k=1, 2 ... M) assigned as time series, wherein sub-areas of the camera sensor are summarized by reading out lines of the camera sensor, which lie parallel to the connection axis between the illumination unit and the camera sensor and along which the distance from the illumination unit increases, and parallel rows are combined into a single averaged row, and the data processing means is arranged to evaluate the averaged row as a function of the distance from the illumination to muscle oximetry.

2. Device according to claim 1, wherein the data processing unit is adapted to read out each line of the camera sensor, which run parallel to the connecting line between the illumination unit and the camera sensor and (for summarizing the sub-areas of sensor elements) to average all lines to an average line intensity $$\bar{I}(i)_{\lambda m}(n, t_k) = \frac{1}{N_Z}\sum_{a=0}^{N_Z} I_a(i)_{\lambda m}(n, t_k)$$

where i=1,2 ... $N_{Sp}$ is the continuous column index and $N_{Sp}$ is the number of columns of the camera sensor and the index λm symbolizes the wavelength of the emission maximum of the respective LED type and as averaged intensity $\bar{I}(i)_{\lambda m}(n, t_k)$ of the respective activation sequence n from the sequence n=1, 2 ... N of activation sequences and the respective activation start time $t_k$ (k=1, 2 ... M) are recorded as time series.

3. Device according to claim 1, wherein the data processing unit is set up to add up the intensities of the sensor elements over all lines and columns to a via the camera sensor integrated camera sensor intensity $$\bar{I}_{\lambda m} = \frac{1}{N_Z \cdot N_{Sp}}\sum_{a=0}^{N_Z}\sum_{i=0}^{N_{Sp}} I_a(i)_{\lambda m}$$

where i=1, 2 ... $N_{Sp}$ symbolizes the continuous column index, $N_{Sp}$ the number of columns of the camera sensor, a the continuous line index, $N_Z$ the number of lines of the camera sensor and the index λm the wavelength of the emission maximum of the respective LED type, and to record these as time series $\bar{I}_{\lambda m}(n, t_k)$ of the camera sensor intensity, assigned to the respective activation sequence n from the sequence n=1, 2 ... N of activation sequences and the respective activation start time $t_k$ (k=1, 2 ... M).

4. Device according to claim 3, wherein the data processing unit is adapted to add up the time series $\bar{I}_{\lambda m}(n, t_k)$ of the camera sensor intensity of the different wavelengths λ1, λ2 ... λL to a wavelength-spanning individual time series $\bar{I}(n, t_k)$ of the camera sensor intensity and to record it.

5. Device according to claim 1, wherein the illumination unit comprises at least one LED type with emission maximum in the range of 500 nm to 540 nm and an LED type with emission maximum in the range of 570 nm to 585 nm.

6. Device according to claim 5, wherein the illumination unit in the NIR wavelength range comprises at least three different LED types whose emission maxima span an NIR wavelength range from 600 nm to 1100 nm.

7. Device according to claim 6, wherein the illumination unit in the spanned NIR wavelength range comprises at least four different LED types with emission maxima distributed in the spanned NIR wavelength range.

8. Device according to claim 1, wherein the illumination unit in the NIR wavelength range has a plurality of LED types with emission maxima distributed in the wavelength range 800-1100 nm, including an LED type with emission maximum at 960 nm, an LED type with emission maximum at 930 nm, and at least two LED types with emission maxima in the range of 790-920 nm, and that the data processing unit is adapted to determine from the absorption measured at 960 nm the concentration of water, taking into account the absorption by fat at 930 nm and the absorption by hemoglobin by evaluating a plurality of absorptions in the range 790-920 nm.

9. Device according to claim 4, wherein the data processing unit is adapted to subject the time series of the wavelength-overlapping camera sensor intensity $\bar{I}(n, t_k)$ of a Fourier transform and to search—for detection of the pulse signal—a distribution peak at a fundamental frequency, which is accompanied by one or more distribution peaks of harmonics at integer multiples of the fundamental frequency.

10. Device according to claim 9, that wherein the data processing unit is adapted to confirm the correctness of detection after detection of a pulse signal, if in the signal of the camera sensor intensity $\bar{I}_{\lambda m}(n, t_k)$ with λm from the wavelength range of 570-585 nm a stronger pulsating signal with the fundamental frequency can be found than in the signal of the camera sensor intensity $\bar{I}_{\lambda m}(n, t_k)$ with λm from the wavelength range of 500-540 nm.

11. Device according to claim 9, wherein the data processing unit is adapted to apply in the Fourier spectrum of the wavelength-overlapping camera sensor intensity $\bar{I}(n, t_k)$ a dynamic band pass filter for the pulse signal detection, wherein the centre of the accepted frequency band is at the detected fundamental frequency and the width of the frequency band is predetermined, wherein the dynamic band pass filter follows the changes of the detected fundamental frequency of the pulse signal if the changed fundamental frequency is within the accepted frequency band, and wherein a hypothetically newly detected pulse signal with its fundamental frequency is discarded if it is outside the accepted frequency band.

12. Device according to claim 9, wherein the data processing unit is set up to assign in the Fourier spectrum of the wavelength-overlapping camera sensor intensity $\bar{I}(n, t_k)$ a distribution peak with a fundamental frequency, which does not have accompanying harmonics with distribution peaks at integer multiples of the fundamental frequency and which is smaller than the frequency of the pulse signal, to the respiration and to determine therefrom the respiration rate.

13. Device according to claim 12, wherein the data processing unit is adapted to apply a dynamic band pass filter in the Fourier spectrum for respiratory signal detection, wherein the center of the frequency band is at the detected respiration rate and the width of the frequency band is predetermined, wherein the dynamic band pass filter goes along with changes of the detected respiration rate if the changed respiration rate is within the accepted frequency band and wherein a hypothetically newly detected respiratory signal with its new respiration rate is discarded if it is outside the accepted frequency band.

14. Device according to claim 3, wherein the data processing unit is set up to evaluate the time series $\bar{I}(i)_{\lambda m}(n, t_k)$ of the camera sensor intensity for emission maxima λm in the NIR wavelength range in relation to each other and in their dependencies on the distance from the illumination unit to determine the degree of oxygenation of the muscle.

15. Method for the continuous and non-invasive determination of physiological parameters of a test person during exercise, in which An LED-based illumination unit, having a plurality of different, juxtaposed LED types whose emission maxima at different wavelengths λ1, λ2 ... λL are from the visible to the NIR wavelength range, is brought in contact with the skin of the test person to a desired measuring point, A photo sensor is placed in contact with the skin of the test person in proximity of the illumination unit in order to detect light, emitted by the illumination unit and passing through the body of the person to an exit location in the area of the photo sensor, A data processing unit, which is connected to the reading unit of the photo sensor for reading it out and which is in communication with the lighting unit, which activates each of the different LED types individually in a predetermined activation sequence at successive activation start times $t_k$ (k=1, 2 ... M) for a respective predetermined activation period and repeats as a result the activation sequence at a clock frequency n=1, 2 ... N of activation sequences, wherein the clock frequency is sufficiently high to dissolve the pulse of the test person's blood circulation, wherein in each activation sequence at least one LED type is activated with an emission maximum below 590 nm, wherein A camera sensor based on CCD or CMOS with a two-dimensional array of sensor elements is used as the photo sensor, The camera sensor is positioned towards the illumination unit so as to rest on the skin on the same side of the body portion as the illumination unit and adjacent thereto to capture the light which gets by transflection through the body of the test person to the camera sensor, The data processing unit reads out the camera sensor in each activation sequence at the activation start times $t_k$ (k=1, 2 ... M) and over the respective activation period and combines the detected intensities of the sensor elements via subregions of sensor elements and assigns the respective activation sequence from the sequence n=1, 2 ... M of activation sequences and the respective activation start time $t_k$ (k=1, 2 ... M) and records them as a time series, wherein subareas of the camera sensor are combined by reading lines of the camera sensor which are parallel to the connection axis between the illumination unit and the camera sensor, and along which the distance from the illumination unit increases, and parallel lines are combined into a single averaged row, and the data processing device is arranged to evaluate the averaged line as a function of the distance from the illumination unit to the muscle oximetry.

* * * * *